United States Patent [19]

Hansen et al.

[11] Patent Number: 5,672,418

[45] Date of Patent: *Sep. 30, 1997

[54] PARTICLE BINDERS

[75] Inventors: Michael R. Hansen, Seattle; Richard H. Young, Sr., Renton, both of Wash.

[73] Assignee: Weyerhaeuser Company, Federal Way, Wash.

[*] Notice: The term of this patent shall not extend beyond the expiration date of Pat. No. 5,308,896.

[21] Appl. No.: 107,469

[22] Filed: Aug. 17, 1993

Related U.S. Application Data

[63] Continuation-in-part of Ser. No. 931,059, Aug. 17, 1992, Pat. No. 5,543,215, Ser. No. 931,277, Aug. 17, 1992, Pat. No. 5,538,783, Ser. No. 931,213, Aug. 17, 1992, Pat. No. 5,300,192, Ser. No. 931,278, Aug. 17, 1992, Pat. No. 5,352, 480, Ser. No. 931,284, Aug. 17, 1992, Pat. No. 5,308,896, and Ser. No. 931,279, Aug. 17, 1992.

[51] Int. Cl.$^6$ .................................................. B32B 5/16
[52] U.S. Cl. ......................... 428/283; 428/288; 428/378; 428/913
[58] Field of Search ........................ 428/283, 288, 428/375, 378, 393, 913

[56] References Cited

U.S. PATENT DOCUMENTS

| | | |
|---|---|---|
| 2,601,597 | 6/1952 | Daniel, Jr. et al. . |
| 2,953,187 | 9/1960 | Francis, Jr. . |
| 3,010,161 | 11/1961 | Duvall . |
| 3,021,242 | 12/1962 | Touey . |
| 3,059,313 | 10/1962 | Harmon . |

(List continued on next page.)

FOREIGN PATENT DOCUMENTS

| | | |
|---|---|---|
| 729513 | 6/1962 | Canada . |
| 806352 | 4/1964 | Canada . |
| 813616 | 12/1965 | Canada . |
| 841940 | 12/1965 | Canada . |
| 953 890 | 9/1974 | Canada . |
| 1052156 | 12/1976 | Canada . |
| 122042 | 10/1984 | European Pat. Off. . |
| 0 427 316 A2 | 7/1989 | European Pat. Off. . |
| 0 427 317 A2 | 7/1989 | European Pat. Off. . |
| 0 429 112 A2 | 7/1989 | European Pat. Off. . |
| 0 440 472 A1 | 1/1990 | European Pat. Off. . |
| 0 442 185 A1 | 8/1991 | European Pat. Off. . |
| 1 382 716 | 2/1964 | France . |
| 489 308 | 1/1930 | Germany . |
| 1 079 796 | 6/1962 | Germany . |
| 2 048 721 | 6/1971 | Germany . |
| 61-28422 | 2/1986 | Japan . |
| 1 217 452 | 12/1969 | United Kingdom . |
| 2189127 | 10/1987 | United Kingdom . |
| WO88/01316 | 2/1988 | WIPO . |
| WO90/09236 | 8/1990 | WIPO . |
| WO90/11181 | 10/1990 | WIPO . |

OTHER PUBLICATIONS

Gugliemelli et al., "Base–Hydrolyzed Starch–Polyacrylonitrile (S–PAN) Graft Copolymer. S–PAN–1:1, PAN M.W. 794,000*," J. of Applied Copolymer Science, 13:2007–2017 (1969).

(List continued on next page.)

Primary Examiner—Christopher Raimund
Attorney, Agent, or Firm—Christensen O'Connor Johnson & Kindness PLLC

[57] ABSTRACT

A binder is applied to fibers to bind particles to the fibers. The fibers have hydrogen bonding functional groups. The particles have functional groups capable of forming a hydrogen bond or a coordinate covalent bond. The binder comprises binder molecules, the binder molecules having at least one functional group that is capable of forming a hydrogen bond or a coordinate covalent bond with the particles, and at least one functional group that is capable of forming a hydrogen bond with the fibers. A substantial portion of the particles that are adhered to the fibers are adhered in particulate form by hydrogen bonds or coordinate covalent bonds to the binder, and the binder is in turn adhered to the fibers by hydrogen bonds. Fibers containing particles bound by this method are easily densified.

36 Claims, 9 Drawing Sheets

U.S. PATENT DOCUMENTS

| | | |
|---|---|---|
| 3,070,095 | 12/1962 | Torr. |
| 3,087,833 | 4/1963 | Drelich. |
| 3,327,708 | 6/1967 | Sokolowski. |
| 3,344,789 | 10/1967 | Arnold et al.. |
| 3,377,302 | 4/1968 | Gugliemelli et al.. |
| 3,395,201 | 7/1968 | Kalwaites. |
| 3,425,971 | 2/1969 | Gugliemelli et al.. |
| 3,494,992 | 2/1970 | Wiegand. |
| 3,521,638 | 7/1970 | Parrish. |
| 3,554,788 | 1/1971 | Fechillas. |
| 3,661,154 | 5/1972 | Torr. |
| 3,661,632 | 5/1972 | Gagliardi et al.. |
| 3,669,103 | 6/1972 | Harper et al.. |
| 3,670,731 | 6/1972 | Harmon. |
| 3,672,945 | 6/1972 | Taylor. |
| 3,692,622 | 9/1972 | Dunning. |
| 3,745,060 | 7/1973 | Jumentier et al.. |
| 3,766,922 | 10/1973 | Krusko. |
| 3,777,758 | 12/1973 | Mesek et al.. |
| 3,788,936 | 1/1974 | Brock et al.. |
| 3,804,092 | 4/1974 | Tunc. |
| 3,808,088 | 4/1974 | Knechtges et al.. |
| 3,886,941 | 6/1975 | Duane et al.. |
| 3,888,256 | 6/1975 | Studinger. |
| 3,888,257 | 6/1975 | Cook et al.. |
| 3,901,236 | 8/1975 | Assarsson et al.. |
| 3,903,889 | 9/1975 | Torr. |
| 3,908,659 | 9/1975 | Wehrmeyer et al.. |
| 3,923,592 | 12/1975 | George et al.. |
| 3,949,035 | 4/1976 | Dunning et al.. |
| 3,978,257 | 8/1976 | Ring. |
| 3,991,237 | 11/1976 | Topfl et al.. |
| 4,007,083 | 2/1977 | Ring et al.. |
| 4,009,313 | 2/1977 | Crawford et al.. |
| 4,035,217 | 7/1977 | Kennette et al.. |
| 4,055,180 | 10/1977 | Karami. |
| 4,061,268 | 12/1977 | Demaster. |
| 4,062,451 | 12/1977 | Gander. |
| 4,071,636 | 1/1978 | Nishino et al.. |
| 4,102,340 | 7/1978 | Mesek et al.. |
| 4,103,062 | 7/1978 | Aberson et al.. |
| 4,160,059 | 7/1979 | Samejima. |
| 4,232,674 | 11/1980 | Melican. |
| 4,250,660 | 2/1981 | Kitamura et al.. |
| 4,282,121 | 8/1981 | Goodrich. |
| 4,287,536 | 9/1981 | Dereser. |
| 4,289,513 | 9/1981 | Brownhill et al.. |
| 4,324,706 | 4/1982 | Tabe et al.. |
| 4,364,992 | 12/1982 | Ito et al.. |
| 4,379,194 | 4/1983 | Clarke et al.. |
| 4,394,172 | 7/1983 | Scheuble et al.. |
| 4,404,250 | 9/1983 | Clarke. |
| 4,410,571 | 10/1983 | Korpman. |
| 4,412,036 | 10/1983 | Pederson et al.. |
| 4,424,247 | 1/1984 | Erickson. |
| 4,457,978 | 7/1984 | Wawzonek. |
| 4,467,012 | 8/1984 | Pederson et al.. |
| 4,486,501 | 12/1984 | Holbek. |
| 4,492,729 | 1/1985 | Bannerman et al.. |
| 4,532,176 | 7/1985 | Briggs et al.. |
| 4,537,767 | 8/1985 | Rothman et al.. |
| 4,558,091 | 12/1985 | Hubbard. |
| 4,597,930 | 7/1986 | Szal. |
| 4,673,402 | 6/1987 | Weisman et al.. |
| 4,676,784 | 6/1987 | Erdman et al.. |
| 4,758,466 | 7/1988 | Dabi et al.. |
| 4,772,492 | 9/1988 | Bouchette. |
| 4,788,080 | 11/1988 | Hojo et al.. |
| 4,818,599 | 4/1989 | Marcus. |
| 4,826,880 | 5/1989 | Lesniak et al.. |
| 4,833,011 | 5/1989 | Horimoto. |
| 4,842,593 | 6/1989 | Jorden et al.. |
| 4,874,811 | 10/1989 | Borchers et al.. |
| 4,886,697 | 12/1989 | Perdelwitz, Jr. et al.. |
| 4,892,769 | 1/1990 | Perdelwitz, Jr. et al.. |
| 4,902,565 | 2/1990 | Brook. |
| 5,002,814 | 3/1991 | Knack et al.. |
| 5,057,166 | 10/1991 | Young, Sr. et al.. |
| 5,064,689 | 11/1991 | Young, Sr. et al. ............ 427/202 |
| 5,128,082 | 7/1992 | Makoui. |
| 5,161,686 | 11/1992 | Weber et al.. |
| 5,217,445 | 6/1993 | Young et al. ............ 604/381 |
| 5,225,047 | 7/1993 | Graef et al. ............ 162/9 |
| 5,230,959 | 7/1993 | Young, Sr. et al. ............ 428/372 |
| 5,252,275 | 10/1993 | Sultze et al. ............ 264/119 |
| 5,252,340 | 10/1993 | Honeycutt ............ 424/489 |
| 5,278,222 | 1/1994 | Stack ............ 524/502 |
| 5,283,123 | 2/1994 | Carter et al. ............ 428/403 |
| 5,300,054 | 4/1994 | Feist et al. ............ 604/378 |
| 5,300,192 | 4/1994 | Hansen et al. ............ 162/184 |
| 5,312,522 | 5/1994 | Van Phan et al. ............ 162/111 |

OTHER PUBLICATIONS

Weaver et al., "Hydrolyzed Starch–Polyacrylonitrile Graft Copolymers: Effect of Structure on Properties*," J. of Applied Polymer Science, 15:3015–3024 (1971).

Weaver et al., "Highly Absorbent Starch–Based Polymer," Northern Regional Research Laboratory, Agricultural Research Service, U.S. Dept. of Agriculture, Peoria, Illinois, pp. 169–177.

"Super slurpers: Time for change?," Chemical Week, pp. 21–22 (Jul. 24, 1974).

S. Lammie, "Use of Glycerine as a Softener for Paper Products," The World's Paper Trade Review, Dec. 13, 1962, p. 2050.

Lindsay, "Absorbent Starch Based Co–polymers—Their Characteristics and Applications," Formed Fabrics Industry, pp. 20, 24 and 26 (May 1977).

Burkholder, "Absorbent Polymers—A New Concept in Fluid Absorption," The Dow Chemical Company Designed Products Laboratory, Midland, Michigan, pp. 73–79 (1973).

Lysogorskaya et al., "Effect of Moisture Content on the Development of Interfiber Bonds in Air–Laid Paper," Leningrad Technological Institute of the Pulp and Paper Industry, Zh. Prikl. Khim., 63:(8) 1869–1872 (1990).

Ogurtsov et al., "Effect of the modulus of elasticity of the binder on the properties of dry–process paper," Sb. Tr. Tsentr. Nauch.–Issled. Inst. Bumagi, 9:123–127 (1974).

Amosov et al., "Aluminum hydroxy compounds—binders for dry–process paper," Izv. VUZ, Lesnoi Zh., 6:72–76 (1986).

Gorbushin e al., "Investigation of the effect of the nature and concentration of binders on the properties of dry–process paper," Sb. Tr. Tsentr. Nauch.–Issled. Inst. Bugami, 9:117–123 (1974).

Hogue et al., "Granulation and Tabletting of Iron Oxide–Chromic Oxide Catalyst Mass with the Aid of Binding Ingredients Part II–Cellulosic Derivatives and Polyethylene Glycol as Binding Ingredients," Fertilizer Technology, 20:30–35 (1983).

Lysogorskaya et al., "Effect of Moisture Content on Development of Interfiber Bonding in the Structure of Air–Dried Paper," Plenum Publ. Corp., pp. 1730–1733 (1991).

Sliwiok and Kowalska, "Investigation of Self–Association of the Selected Glycols and Cellulose Sorbents," Microchemical Journal, 26:68–74 (1981).

Blanchard and Reinhart, "Dyeing of Crosslinked Cotton Containing Glycol Additives," U.S. Dept. of Agriculture, New Orleans, 24:13–17 (Jan. 1992).

Byrd, "How bonds develop during web consolidation," PTI, pp. 240–243 (Oct. 1986).

FIG. 6
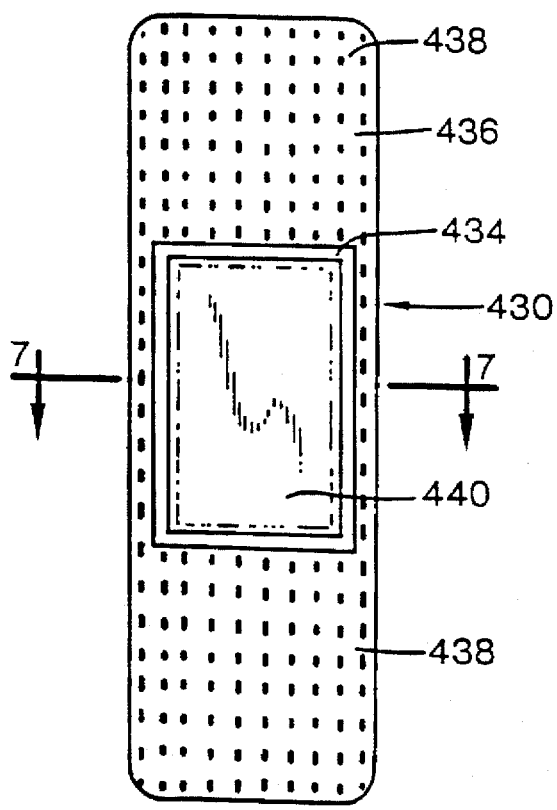
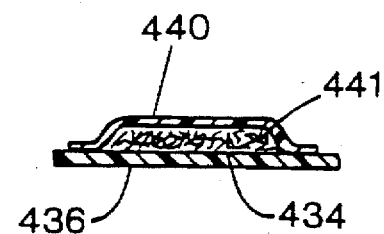
FIG. 7

PARTICLE BINDERS

CROSS REFERENCE TO RELATED APPLICATIONS

This is a continuation-in-part application of the following U.S. Patent Applications, each of which was filed on Aug. 17, 1992, and each of which is hereby incorporated herein by reference: (1) Ser. No. 07/931,059, entitled "POLYMERIC BINDERS FOR BINDING PARTICLES TO FIBERS", now U.S. Pat. No. 5,543,215; (2) Ser. No. 07/931,277, entitled "NON-POLYMERIC ORGANIC BINDERS FOR BINDING PARTICLES TO FIBERS", now U.S. Pat. No. 5,538,783; (3) Ser. No. 07/931,213, entitled "WET LAID FIBER SHEET MANUFACTURING WITH REACTIVATABLE BINDERS FOR BINDING PARTICLES TO BINDERS", now U.S. Pat. No. 5,300,192; (4) Ser. No. 07/931,278, entitled "REACTIVATABLE BINDERS FOR BINDING PARTICLES TO FIBERS", now U.S. Pat. No. 5,352,480; (5) Ser. No. 07/931,284, entitled "PARTICLE BINDERS FOR HIGH BULK FIBERS", now U.S. Pat. No. 5,308,896; and (6) Ser. No. 07/931,279, entitled "PARTICLE BINDERS THAT ENHANCE FIBER DENSIFICATION", pending.

FIELD OF THE INVENTION

This invention concerns binders for fibers and the use of such binders in binding particles to fibers. The fibers and bound particles may be easily densified by external application of pressure. The binders are reactivatable, and may be applied to fibers on a wet-laid fiber sheet manufacturing line. In particular embodiments, the invention concerns binding superabsorbent particles to cellulosic fibers, which may then be used, for example, to make absorbent fibers that are densified and incorporated into absorbent products. In other embodiments, the invention concerns the reactivation and use of such fibers, preferably at an article manufacturing plant, at a location remote from a pulp sheet manufacturing line to bind superabsorbent and/or other particles to cellulosic fibers which may then be used, for example, as absorbent fibers incorporated into absorbent products.

BACKGROUND OF THE INVENTION

Superabsorbent polymers have been developed in recent years that are capable of absorbing many times their own weight of liquid. These polymers, which are also known as water insoluble hydrogels, have been used to increase the absorbency of sanitary products such as diapers and sanitary napkins. Superabsorbent polymers are often provided in the form of particulate powders, granules, or fibers that are distributed throughout absorbent cellulosic products to increase the absorbency of the product. Superabsorbent particles are described, for example, in U.S. Pat. No. 4,160,059; U.S. Pat. No. 4,676,784; U.S. Pat. No. 4,673,402; U.S. Pat. No. 5,002,814; and U.S. Pat. No. 5,057,166. Products such as diapers that incorporate absorbent hydrogels are shown in U.S. Pat. No. 3,669,103 and U.S Pat. No. 3,670,731.

One problem with the use of superabsorbents is that the superabsorbent material can be physically dislodged from the cellulosic fibers of an absorbent product. Separation of the superabsorbent from its substrate reduces the absorbency of the product and diminishes the effectiveness of the superabsorbent material. This problem was addressed in European Patent Application 442 185 A1, which discloses use of a polyaluminum chloride binder to bind an absorbent polymer to a fibrous substrate. The polyaluminum binder, however, suffers from the drawback of being an inorganic product that is not readily biodegradable. Moreover, that European patent does not offer any guidance for selecting binders other than polyaluminum chloride that would be useful in binding absorbent particles.

A method of immobilizing superabsorbents is disclosed in U.S. Pat. No. 4,410,571 in which a water swellable absorbent polymer is converted to a non-particulate immobilized confluent layer. Polymer particles are converted to a coated film by plasticizing them in a polyhydroxy organic compound such as glycerol, ethylene glycol, or propylene glycol. The superabsorbent assumes a non-particulate immobilized form that can be foamed onto a substrate. The individual particulate identity of the superabsorbent polymer is lost in this process. The confluent nature of the superabsorbent material can also result in gel blocking, in which absorption is diminished as the water swollen polymers block liquid passage through the film layer.

U.S. Pat. No. 4,412,036 and U.S. Pat. No. 4,467,012 disclose absorbent laminates in which a hydrolyzed starch polyacrylonitrile graft copolymer and glycerol mixture is laminated between two tissue layers. The tissue layers are laminated to each other by applying external heat and pressure. The reaction conditions form covalent bonds between the tissue layers that firmly adhere the tissue layers to one another.

Numerous other patents have described methods of applying binders to fibrous webs. Examples include U.S. Pat. No. 2,757,150; U.S. Pat. No. 4,584,357; and U.S. Pat. No. 4,600,462. Such binders are not described as being useful in binding particulates, such as superabsorbent particles, to fibers. Yet other patents disclose crosslinking agents such as polycarboxylic acids that form covalent intrafiber bonds with individualized cellulose fibers, as in European Patent Application 440 472 A1; European Patent Application 427 317 A2; European Patent Application 427 316 A2; and European Patent Application 429 112 A2. The covalent intrafiber bonds are formed at elevated temperatures and increase the bulk of cellulose fibers treated with the crosslinker by forming intrafiber ester crosslinks. Crosslinking must occur under acidic conditions to prevent reversion of the ester bonds. The covalent bonds within the fibers produce a pulp sheet that is more difficult to compress to conventional pulp sheet densities than in an untreated sheet. Covalent crosslink bonds may also form between the fibers and particles, and occupy functional groups that would otherwise be available for absorption, hence absorption efficiency is decreased.

A particular disadvantage of forming covalent ester intrafiber crosslinks is that the resulting fiber product resists densification. Energy requirements for making densified absorbent products are increased because very high compression pressures must be used to densify the absorbent product. It would be advantageous to provide a method of enhancing densification of crosslinked fibers by reducing energy requirements for densification.

Many different types of particles other than superabsorbents may be added to fibers for different end uses. Antimicrobials, zeolites and fire retardants are but a few examples of particles that are added to fibers. It would be advantageous to provide a method of attaching particles that could be accommodated to the many different particle needs of end users. Moreover, it would be advantageous to reduce particulate waste in the attachment process, and simplify shipment of fiber products that require particulate addition. It would be further advantageous to bind particulates to fibers without requiring the shipment of bulk fibers with adhered particulates because shipping and excessive handling of these fibers subject them to mechanical impact which can dislodge some particles from the fibers. It would also be advantageous to incorporate binders onto fibers during the initial pulp sheet manufacturing process so that the fibers are ready for reactivation and use at a remote product manufacturing location.

It has previously been important that particles added to cellulose products be insoluble in liquids such as water or liquid binders. It has been thought that liquid insolubility (particularly water insolubility) was an essential characteristic for particles bound to cellulose fibers because soluble particles would be dissolved by a water containing binder. Although the particle could eventually resolidify as the binder evaporated, dissolution of the particle in the binder would cause the particle to diffuse to areas of the product where it was not needed or desired. Water soluble particles have therefore not been used for particles that were to be bound to fibers using a binder.

SUMMARY OF THE INVENTION

The foregoing and other problems have been overcome by providing fibers with hydrogen bonding functional sites, and binders that have a volatility less than water. The binder comprises binder molecules. The binder molecule has at least one functional group that is capable of forming a hydrogen bond with the fibers, and at least one functional group that also is capable of forming a hydrogen bond or a coordinate covalent bond with particles that have a hydrogen-bonding or coordinate-covalent bonding functionality.

The fibers of the present invention may have particles bound to the fibers with a binder. The binder may be selected from the group consisting of glycerin, a glycerin monoester, a glycerin diester, a propylene glycol, a propylene glycol oligomer, a polyglycerin oligomer, urea, and combinations thereof. As used herein, an oligomer refers to a condensation product of polyols, wherein the condensation product contains less than ten monomer units. A polyglycerin oligomer as referred to herein means a condensation product of two or more glycerin molecules. A propylene glycol oligomer as referred to herein means a condensation product of two or more propylene glycol molecules. The binder also may be selected from the group consisting of glycerin, a glycerin monoester, a glycerin diester, a propylene glycol, a propylene glycol oligomer, a polyglycerin oligomer, and combinations thereof. The binder also may be selected from the group consisting of glycerin and urea, or may be selected from the group consisting of a glycerin monoester and a monoglyceride, or a glycerin diester or a diglyceride. At this time, specifically preferred non-polymeric binders are glycerin and urea.

As stated above, the binders include glycerin esters. An ester is defined generally as being derived from an acid (either inorganic or organic) by the exchange of the replaceable hydroxl group of the acid for an organic group. The usual reaction is that of an acid (organic or inorganic) with an alcohol or other organic compound having at least one hydroxyl group. For the present invention, glycerin esters are used. Glycerin is a triol, and hence is a compound that is rich in hydroxyl groups. Glycerin may form esters at each of its three hydroxyl groups. However, for the present invention, one of the hydroxyl groups preferably is not esterified, so that particularly suitable glycerin esters for the present invention include glycerin monoesters and glycerin diesters.

Virtually any compound that can react with glycerin (an esterifying compounds) to form an ester can be used to produce the binders of the present invention, as long as such esterifying compounds subsequently enable the binder to form hydrogen bonds with the fibers, and either hydrogen bonds or coordinate covalent bonds with the particle. The organic esterifying compounds preferably include a functional group that is selected from the group, without limitation, consisting of a carboxyl (for example, carboxylic acids), a carboxylate, a carbonyl (for example, aldehydes), a sulfonic acid, a sulfonate, a phosphoric acid, a phosphate, an amide, an amino, a hydroxyl (such as an alcohol) and combinations thereof (for example, an amino acid or an hydroxy acid). The esterifying compound also can be an inorganic acid, such as, without limitation, a phosphoric acid, a phosphate, a sulfuric acid, a sulfate, a nitric acid, a boric acid, and a borate.

The binder molecule has at least one functional group that is capable of forming a hydrogen bond or at least one coordinate covalent bond with particles, and at least one functional group that is capable of forming a hydrogen bond with the fibers.

Particularly preferred binders include those that can form five or six membered rings, most preferably six membered rings, with a functional group on the particle surface. At present, glycerin, glycerin monoesters, glycerin diesters, propylene glycol, propylene glycol oligomers, polyglycerol oligomers, and blends of these with urea, are the preferred binders. At this time, a specifically preferred binders are glycerin and urea.

The fibrous material may be cellulosic or synthetic fibers that are capable of forming hydrogen bonds with the binder, while the particles are selected to be of the type that are capable of forming hydrogen bonds or coordinate covalent bonds with the binder. It has unexpectedly been found that this binder system secures particles to fibers exceptionally well. A superior fibrous product is therefore produced that has improved absorbent properties as compared to unbound or covalently bound particles. Formation of the noncovalent bond allows production of a fiber product that is easily manufactured and a web that is easily densified, and that is readily biodegradable and disposable.

In one preferred embodiment, an absorbent product comprises a fibrous cellulosic mat that contains superabsorbent hydrogel particles in particulate form. The superabsorbent particles form hydrogen bonds or coordinate covalent bonds with the binder, depending upon the binder, while the binder in turn forms hydrogen bonds with the hydroxyl groups of the cellulose fibers. These noncovalent, relatively flexible bonds between the binder and particles maintain the particles in contact with the fibers, and resist dislodgement of the particles by mechanical forces applied to the mat during manufacture, storage or use. The amount of binder present typically depends on a number of factors, including the nature of the binder and particles, and whether the particles are immediately added to the fibers or after a period of time. Hence, one skilled in the art will realize that the amount of binder suitable and particularly useful for a particular application will vary. However, the binder may suitably be present in an amount of from about 1 to 80 percent of the total weight of the fibrous material. An especially suitable range of binder is 1 to 40 percent by weight, or 1 to 25 percent by weight of the fibrous material. The particles bound by the binder of the present invention (via hydrogen/ coordinate covalent bonds) may suitably be present in an amount of 0.05 to 80 percent, preferably 1 to 80 percent or 3 to 80 percent, or more than 3 percent by weight of the total weight of the fibrous material and the particles. A particularly suitable range of particles is 3 to 60 percent by weight of the fibrous material and particles. A preferred weight ratio of particle to binder is 2:1 to 40:1. An example of a suitable particle is a superabsorbent polymer such as a starch graft polyacrylate hydrogel fine or larger size particle such as a granule, which forms hydrogen bonds with the binder. The binder also forms hydrogen bonds with the hydroxyl groups of the cellulose, thereby securely attaching the superabsorbent particles to the fibers.

The present invention also includes a method of binding particles to fibers wherein the particles are insoluble in the binder (and soluble in water) and therefore retain their solid particulate form following binding. The particles, whether or not water soluble, preferably have functional groups that can form hydrogen bonds or coordinate covalent bonds with the binder, and the binder in turn is capable of forming hydrogen bonds to the fibers. Other particles without the desired functionality also may be included in the fiber product, but such particles will not be bound as strongly in the same manner.

In especially preferred embodiments, the fibers are cellulosic and the particles are superabsorbent particles that are bound to the binder by hydrogen bonds. The fibers also may be continuous or discontinuous synthetic or natural fibers having a hydrogen-bonding functional group that hydrogen bonds with the binder. The binder is suitably applied to the fibers in an amount of at least 1 percent, and preferably no more than 80 percent, by total weight of the fibrous material. The particles may be bound to the fibers at less than 150° C. or without any external application of heat at ambient temperature (e.g., about 25° C.). Particles also may be bound in the absence of any external application of pressure, or in the absence of external heat and pressure.

In some embodiments the binder is associated with the fibers as a solid (for example, a dry powder or a dried liquid), and the fibers contain at least 7 percent water by weight when the binding step is performed. This level of moisture in the fibers provides sufficient mobility of reactants to allow the particles and fibers to bind well to each other. When a liquid binder is used (for example, glycerin), the fibers suitably contain at least about 0.5 percent water by weight. A solid binder is suitably used with fibers having less than 0.5 percent water by weight if the binder is heated above its melting point to liquefy it. A solid binder may be thermoplastic or meltable, such that it can be heated above its melting or softening point and then cooled to fuse fibers to each other. The thermoplastic properties of the binder also can provide additional mechanical adherence between the particles and fibers. In some embodiments, a meltable binder, such as urea, may be employed which can adhere particles both physically and with hydrogen bonding.

In other embodiments, the particles are soluble in water but have reduced solubility in the binder such that the particles can be bound in solid particulate form to the fibers. Addition of the binder does not dissolve the particle and cause it to diffuse away from its desired site of attachment to the fibers.

The binder attaches the particles to the fibers, and forms a bond that has been found to be resistant to mechanical disruption. A significant advantage of these binders is that the binder and particle together on the fiber have been found to reduce the pressure required to densify the fibers.

The binders also can be present on fibers in an inactive state for more than a week, a month, or a even a year, then later activated to bind particles to the fibers. Liquid binders (which include neat liquids or solutions of solid binders) can be placed on the fibers, dried, and later activated by moistening the fibers. Alternatively, a dry solid binder may be added to the fibers and later activated by addition of a liquid. An inactive binder can also be activated by applying kinetic energy to the fibers after the binder and fibers reach an equilibrium moisture content with the atmosphere (hereinafter referred to as "air dry"). Kinetic energy can be applied to the binder and fibers, for example and without limitation, by applying mechanical agitation, pressure from an external source, or using ultrasonics. In yet other embodiments, the binder may be activated by heating the fibers after applying the binder to the fibers.

The capacity for activation allows the binder to be applied to the fibers, which are then shipped to distribution points with the binder in an inactive form. The binder is then activated at the distribution point (for example, a customer's facility) where particles are added to the fibers and bound thereto. As used herein, binder "activation" includes both activation of previously inactive binders (such as solid binders in the absence of liquid) or reactivation of previously active binders (such as a liquid binder that has been dried).

Another advantage of the present invention is that the binder can be activated in a pattern that corresponds to a desired distribution of particles in fibrous material. An activation fluid, such as an activation liquid, for example, can be applied to the areas of a diaper that will be initially moistened by urine during use. Examples, without limitation, of a suitable activation liquid include water, lower-alkyl alcohols, polyols such as the glycols, acetone, and combinations thereof, such as water and glycerin. When the activating fluid is a liquid such as water, the water may be sprayed or otherwise applied and may be provided in the form of steam or moisture-laden gas, such as humid air. Other liquid activation fluids may be applied in the same manner. Superabsorbent particles can be added to activated areas of the diaper and adhered almost exclusively in those areas where initial urine absorption is required. Targeted activation of binder allows particles to be efficiently and economically attached to the fibers, with reduced particle wastage. Moreover, targeted binder activation and particle adherence increases the absorptive efficiency of the product by diminishing excessive wicking of liquid within the plane of an absorptive product.

The invention also is directed to fibrous products produced by any of the methods described herein, and to absorbent articles comprised of such fibrous products. These fibrous products include fibers with inactive or activatable binders. A fibrous product may be individual fibers or webs made thereof.

The present invention relates to the above objects, features and advantages individually as well as collectively. The foregoing and other features and advantages of the invention will become more apparent from the following detailed descriptions and accompanying drawings.

BRIEF DESCRIPTION OF THE DRAWINGS

FIG. 6 illustrates a plan view of a bandage incorporating fibers of the present invention.

FIG. 7 is a sectional view of the bandage of FIG. 6, taken along line 7—7 of FIG. 6.

DETAILED DESCRIPTION OF SEVERAL PREFERRED EMBODIMENTS OF THE INVENTION

I. Processing of Fibers

Figure 1:
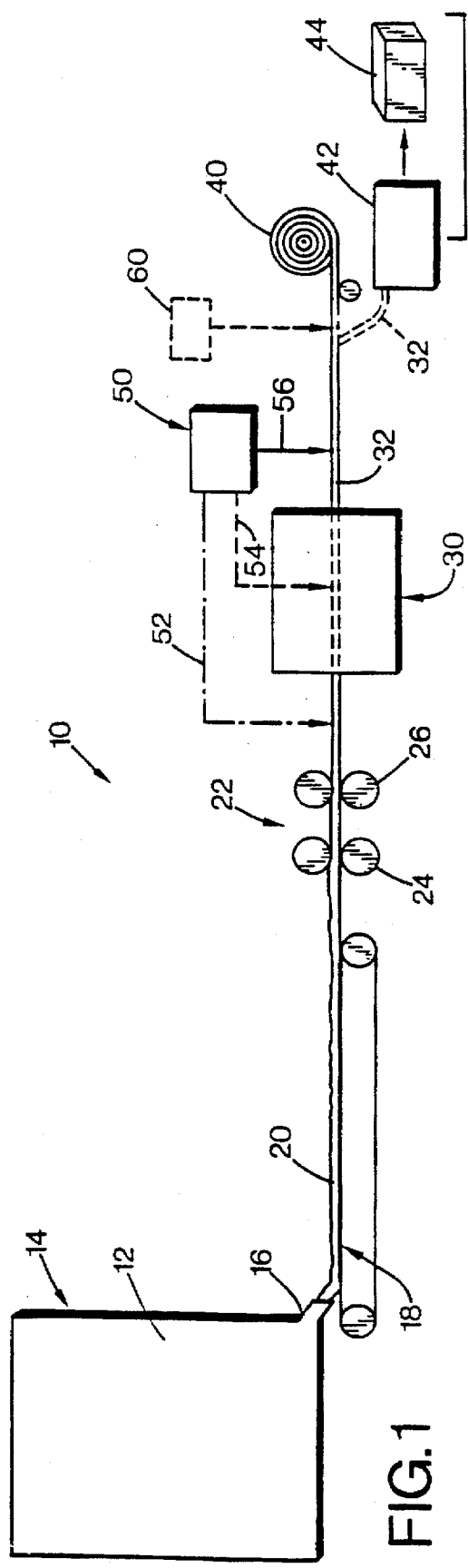
FIG. 1 is a schematic illustration of a wet laid sheet manufacturing line illustrating the application of binders in accordance with the present invention during the manufacture of a fiber sheet.

FIG. 1 illustrates a wet laid sheet manufacturing line such as a pulp sheet manufacturing line 10. In this manufacturing line, a pulp slurry 12 is delivered from a headbox 14 through a slice 16 and onto a Fourdrinier wire 18. The pulp slurry 12 typically includes cellulose fibers such as wood pulp fibers and may also include synthetic or other non-cellulose fibers as part of the slurry. Water is drawn from the pulp deposited on wire 18 by a conventional vacuum system, not shown, leaving a deposited pulp sheet 20 which is carried through a dewatering station 22, illustrated in this case as two sets of calendar rolls 24, 26 each defining a respective nip through which the pulp sheet or mat 20 passes. From the dewatering station, the pulp sheet 20 enters a drying section 30 of the pulp manufacturing line. In a conventional pulp sheet manufacturing line, drying section 30 may include multiple canister dryers with the pulp mat 20 following a serpentine path around the respective canister dryers and emerging as a dried sheet or mat 32 from the outlet of the drying section 30. Other alternate drying mechanisms, alone or in addition to canister dryers, may be included in the drying stage 30. The dried pulp sheet 32 has a maximum moisture content pursuant to the manufacturer's specifications. Typically, the maximum moisture content is no more than 10% by weight of the fibers and most preferably no more than about 6% to 8% by weight. Otherwise, the fibers tend to be too damp. Unless overly damp fibers are immediately used, these fibers are subject to degradation by, for example, mold or the like. The dried sheet 32 is taken up on a roll 40 for transportation to a remote location, that is, one separate from the pulp sheet manufacturing line, such as at a user's plant for use in manufacturing products. Alternatively, the dried sheet 32 is collected in a baling apparatus 42 from which bales of the pulp 44 are obtained for transport to a remote location.

A binder of the type explained in detail below is applied to the pulp sheet from one or more binder applying devices, one of which is indicated at 50 in FIG. 1. Any binder-applying device may be used, such as sprayers, roll coaters, immersion applicators or the like. Sprayers are typically easier to utilize and incorporate into a pulp-sheet manufacturing line. As indicated by the arrows 52, 54 and 56, the binder may be applied at various locations or at multiple locations on the pulp sheet manufacturing line, such as ahead of the drying stage 30 (indicated by line 52), intermediate the drying stage 30 (as indicated by line 54), or downstream from the drying stage 30 (as indicated by the line 56). Solutions of non-volatile binders, such as non-polymeric urea, are typically applied at a location where sufficient drying can still take place in the drying stage to produce a dried binder-containing fiber sheet with no more than the maximum desired moisture content. Consequently, to take advantage of the drying stage 30, solutions of non-volatile binders are typically applied at locations 52 or 54. At location 52, the water remaining in the sheet or mat 20 at this stage tends to interfere with the penetration of the binder into the sheet. Consequently, application of the binder after some drying has taken place, for example at location 54, is preferable. If solutions of non-volatile binders are applied at location 56 in an amount which would cause the moisture content of the sheet to exceed the desired maximum level, an additional drying stage (not shown) may be included in the pulp manufacturing line to bring the moisture content down to the desired level.

A non-aqueous binder, such as glycerin, is most preferably added downstream from the drying stage at location 56 or during the drying stage as indicated by location 54. However, liquid non-aqueous binders also may be added at a location, such as location 52, upstream of the drying stage. At this latter location, the water in the wet web at this point may tend to attract these binders into the mat or sheet as the binders tend to be hydroscopic. Since non-aqueous binders typically do not enhance the degradation of the product due to the addition of moisture to the sheet, they can be applied downstream from the drying stage without bringing the moisture content of the sheet above the desired maximum level.

The particulate materials, selected as explained below, may be added to the sheet and adhered thereto by the binders on the pulp manufacturing line. A suitable particulate applicator is indicated at 60, and may comprise a bulk or volumetric metering device. These particles may be sprinkled, poured or otherwise added to the sheet. To facilitate the adherence of these particulates to the sheet at this location, enough moisture must remain in the sheet, in the case of aqueous binders, to enable the bonding between the particles and fibers as explained below. For non-aqueous binders, the particles in this case are preferably added while the binder is still wet or heated to facilitate the reaction. Particles can be added on the pulp sheet manufacturing line in this manner, with a subsequent drying stage being utilized to reduce the moisture content following particulate addition. However, if a water-based binder makes the fibers too wet following the addition of the particles, this is not the preferred approach.

Although the above approach is advantageous because the particles are strongly bound to the fibers, during transportation of rolls or bales of these fibers it is possible for particles to become dislodged by mechanical impact during transport, fiberization or other subsequent processing. In addition, this approach interferes with the customization of the fiber application at a user's location. For example, a user may want the capability of selecting particular types or brands of particles for adherence to the fibers in the user's products, without having this selection made by a pulp sheet manufacturer who incorporates the particles into the pulp sheet during its manufacture. Also, certain particles may degrade over time, making it advantageous to add such particles immediately prior to incorporation into products. For example, superabsorbent particles are susceptible to absorbing moisture from the atmosphere during shipment. Particles with a relatively short shelf life, such as certain zeolites (e.g. Abscents with odor absorbing materials which can become saturated with odors over time) being one example, may also degrade over time. Another example is zeolites with silver salts as antimicrobial agents, which can photodegrade. Therefore, it is also advantageous to provide a fibrous product in which the end user of the product may incorporate the desired particles at the time the fibers are converted into products.

Figure 2:
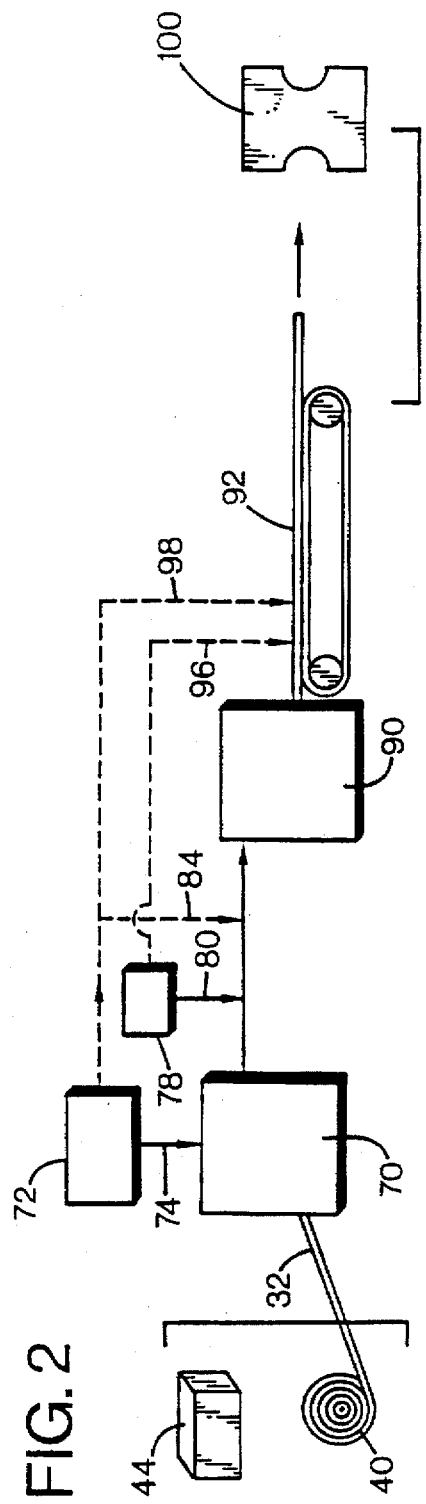
FIG. 2 is a schematic illustration of a binder reactivation and particulate attachment process in accordance with the present invention.

Therefore, in keeping with this latter preferred approach, as illustrated in FIG. 2, the respective rolls 40 or bales 44 of binder-containing fibers, without particles, are transported to a remote location for use by a user. These rolls or bales (or otherwise transported fibers, e.g., bagged, containerized or otherwise in bulk form) are then refiberized by a fiberizing apparatus 70. Although any fiberizer may be used, a typical fiberizing apparatus 70 is a hammermill which may be used alone or in conjunction with other devices such as picker rolls or the like for breaking up the sheet 32 or bales 42 into individual fibers.

A particulate-material adding mechanism 72 (e.g., like mechanism 60) delivers the desired particulate materials to the fibers at the desired location in the user's process. Again, the device 72 typically comprises a metering mechanism, although any suitable device for adding particulates to fibrous materials may be used. For example, the particulates may be delivered as indicated by line 74 to the fiberizing apparatus 70. In the case of some binders, agitation of fibers within the fiberizer 70, as explained in greater detail below, activates the binders and causes the particulates to be adhered to the fibers by the binder. Alternatively, an activating fluid, which may be a liquid such as water, glycerin, lower-alkyl alcohols, polyols such as the glycols, acetone, and combinations thereof, such as water and glycerin, may be sprayed or otherwise applied to the fibers, such as from an activation fluid tank or source 78 by way of a sprayer (not shown) at location 80. The particles may then be applied, as indicated by line 84, to the fibers downstream from the application of the activation liquid 80. Alternatively, the particles which may be added prior to or at location 80, are adhered to the fibers by the binder upon activation of the binder at location 80. Binder also may be combined with the fibers as the particles are added to the fiber sheet.

As yet another alternative, the fiberized fibers are delivered to an air-laying device 90 and reformed into a desired product such as a web indicated at 92. In the case of air-laid fibers, the activation fluid or liquid may be applied to the web at location 96 with the particles then being added at location 98 as shown with the activated binder then adhering the particles to the fibers. The particles may be applied at a location in the process upstream from the application of the activating liquid at location 96. Alternatively, the activating fluid may be added simultaneously with the addition of particles, so that the activation occurs simultaneously with the addition of particles. The activating fluid also may be added after the particles are added to the fibers. In addition, the binder may be activated at specifically defined locations on the web 92, such as in target zones of an absorbent core of a product with the particles then only being applied to these target zones, thereby minimizing the wasting of the particulate material. A specific example of a target zone is the crotch region of a diaper where most diaper wetting would occur. The application of superabsorbent particles to such a zone places these particles at a location where they are most useful in absorbing liquid. The web 92, with or without other components of the end user's product, is then processed into the user's product, such as being included within a disposable diaper 100.

Again, with this approach, the end user of the fibers may readily select particles to be applied to its product and may, if required, activate the binder as required to enhance the efficient production of the user's product. In addition, the user has flexibility in air laying or otherwise combining the binder containing fibers into a finished product with the desired particulates. The binder-containing fibers, because most of the binders are all water soluble, are preferably not wet laid because wet laying would remove at least some of the binder. Not only is handling and shipping of the particulate-containing products avoided by the manufacturer of the pulp sheet, enhanced adhesion of particulates to the fibers results because the particles are not subjected to mechanical forces between the location of manufacture of the fibers and the location at which the particulate materials are added.

II. Fiber Characteristics

The present invention includes a method of binding particles to fibers, and the product, including absorbent end-products, that are produced by such method. In particularly preferred embodiments, the product is a cellulosic or synthetic fiber to which superabsorbent hydrogel polymer particles are adhered by a binder, and absorbent products made therefrom. The invention also includes a combination of wood pulp and certain binders, which for the purpose of this combination are bulk fibers in roll form having a basis weight of at least 350 grams per square meter ($g/m^2$) or bale form. The bulk fiber sheets may have a density of at least about 400 $kg/m^3$. Preferred bulk fibers are wood pulp fibers or softwood pulp fibers. The pulp fibers can be chemical or thermomechanical or chemithermomechanical or combinations thereof. The preferred pulp fiber is chemical. Suitable fibers include wood pulp fibers, which can be obtained from well known chemical processes such as the kraft and sulfite processes. In these processes, the best starting material is prepared from long fiber coniferous wood species, such as pine, douglas fir, spruce and hemlock. Wood pulp fibers can also be obtained from mechanical processes, such as ground wood, mechanical, thermomechanical, chemimechanical, and chemithermomechanical pulp processes. The fibers are preferably elongated, for example having a length to width ratio of about 1000:1 to 5:1.

The fibers of the present invention also include fibers that are pretreated prior to the application of a binder to the fibers. This pretreatment may include physical treatment, such as subjecting the fibers to steam or chemical treatment, such as cross-linking the fibers. Although not to be construed as a limitation, examples of pretreating fibers include the application of fire retardants to the fibers, such as by spraying the fibers with fire retardant chemicals. Specific fire-retardant chemicals include, byway of example, sodium borate/boric acid, urea, urea/phosphates, etc. In addition, the fibers may be pretreated with surfactants or other liquids, such as water or solvents, which modify the surface of the fibers. Other pretreatments include exposure to antimicrobials or pigments.

The fibers also may be pretreated in a way which increases their wettability. The fibers also may be pretreated with conventional cross-linking materials and may be twisted or crimped, as desired. Pretreating cellulose fibers with chemicals which result in lignin or cellulose rich fiber surfaces also may be performed in a conventional manner.

Bleaching processes, such as chlorine or ozone/oxygen bleaching may also be used in pretreating the fibers. In addition, the fibers may be pretreated, as by slurrying the fibers in baths containing various solutions. For example, antimicrobial solutions (such as solutions of antimicrobial particles as set forth below), as well as solutions of fertilizers and pesticides, and/or fragrances and flavors, for release over time during the life of the fibers. Fibers pretreated with other chemicals, such as thermoplastic and thermoset resins also may be used. Combinations of pretreatments also may be employed with the resulting pretreated fibers then being subjected to the application of the binder coating as explained below.

Ground wood fibers, recycled or secondary wood-pulp fibers, and bleached and unbleached wood-pulp fibers can be used. Details of the production of wood pulp fibers are well known to those skilled in the art. These fibers are commercially available from a number of companies, including Weyerhaeuser Company, the assignee of the present invention.

The fibers also can be any of a variety of other natural or synthetic fibers; however, all of the fibers to which particles are attached in accordance with the present invention include a hydrogen-bonding functionality. This does not preclude the blending of such fibers with fibers lacking this characteristic. However, the fibers lacking a hydrogen bonding functionality will not have particles bonded thereto with the strength and manner of the bonds that would be present if the fibers had a hydrogen-bonding functionality.

A hydrogen bond is an intermolecular force that occurs between hydrogen atoms that are covalently bonded to small, strongly electronegative elements (such as nitrogen and oxygen) and nonbonding electron pairs on other such electronegative elements. A hydrogen-bonding functionality is a functional group that contains, an oxygen or nitrogen atom, for example and without limitation, hydroxyls, carboxyls, sulfonic acids, sulfonamides, ethers, esters, epoxides, carbonyls, amines, urethanes and others, that is capable of forming a hydrogen bond. The orbitals of the nonbonding electron pairs on the oxygen or nitrogen overlap with the relatively empty 1s orbital of the hydrogen covalently bonded to another nitrogen or oxygen atom. The is orbital of the hydrogen is relatively empty due to the unequal sharing of the electrons in the covalent bond between it and the small electronegative atom (oxygen or nitrogen) to which it is bound.

Specific examples of natural fibers that contain a hydrogen bonding functionality include chopped silk fibers, wood pulp fibers, bagasse, hemp, jute, rice, wheat, bamboo, corn, sisal, cotton, flax, kenaf, peat moss, and mixtures thereof. Suitable synthetic fibers with hydrogen bonding functionalities include acrylic, polyester, carboxylated polyolefins, rayon and nylon. The hydrogen-bonding functionality is an ester in acrylic fibers and a carboxylic acid in carboxylated polyolefin fibers, an ester in polyester, an amide in nylon, and a hydroxyl in rayon. Polyethylene and polypropylene would be unsuitable fibers for use in particle-to-fiber bonding in the manner of the present invention because they include only carbons and hydrogens without any other atoms, such as oxygens or nitrogens, that can participate in hydrogen bonds.

For purposes of convenience, and not to be construed as a limitation, the following description proceeds with reference to the treatment of individual chemical wood-pulp fibers. The fibers are individualized, for example by defiberization in a hammermill. Such individualized fibers are conventionally formed into a mat, and are commercially available, for example as NB 416 fibers from the Weyerhaeuser Company. Another suitable cellulosic mat would include Rayfloc JLD from ITT Rayonier. The cellulose fibers may be in the form of a cellulosic web or loose cellulose fibers.

III. Particle Characteristics

In accordance with the present invention, particles are added to the fibers to give the fibers desired properties, such as, byway of example only, increased absorbency, abrasiveness, or antimicrobial activity. The particle can be any particulate material that has the desired property and which is capable of forming hydrogen bonds or coordinate covalent bonds with the binder. Hydrogen bonds can be formed, as discussed above, by particles that contain certain functional groups, particularly those having an oxygen or nitrogen. Coordinate covalent bonds, in contrast, are formed by donation of shared pair, hereinafter referred to as a one pair, of electrons on one atom to an empty orbital of another atom. Coordinate covalent bonds differ from covalent bonds in that covalent bonds are formed by a pair of electrons wherein one of the electrons is donated from each of the atoms that participate in the bond. Particles can form coordinate covalent bonds if they have an empty p or d or f orbital that is capable of accepting a pair of electrons from the binder.

A coordinate covalent bond occurs between a donor atom that has a lone pair of electrons to donate to the bond, and an acceptor atom that has an empty orbital to accept the lone pair of electrons from the donor. According to the Aufbau and Pauli principles, electrons occupy the lobes of atomic orbitals one at a time with a maximum of two electrons (with opposite spins) per lobe. The most basic orbital is the s orbital, which is available for bonding the elements in the first row of the periodic table. In the second row of the periodic table, electrons fill first the 2s orbital of Li and Be. However, metals in periods less than three do not have sufficient affinity for electrons to participate in coordinate covalent bonding. Beginning with Group IIIB (boron), the three p orbitals participate in coordinate covalent bonding and the lobes of the p orbitals begin to fill. Boron has one electron in one of the 2p orbitals, thus leaving the other 2p orbitals empty and available for coordinate covalent bonding. An example of a coordinate covalently bonded boron containing particle is boric acid, which is used as an astringent, antiseptic and fire retardant. The boron atom of boric acid may act as an acceptor for a lone pair of electrons donated by an atom of a binder according to the present invention, wherein the atom has a lone pair of electrons. As illustrated above, an oxygen atom of polypropylene glycol (PPG) donates a pair of electrons to boric acid, thereby forming a coordinate covalent bond between a boric acid particle and a PPG binder. The same may hold true for the oxygen atoms of the glycerin and glycerin-ester binders of the present invention. The depiction of boric acid shown below is not typical of the aqueous chemistry of boron, but rather is provided to illustrate the type of bonding that is believed to occur in a coordinate covalent bond.

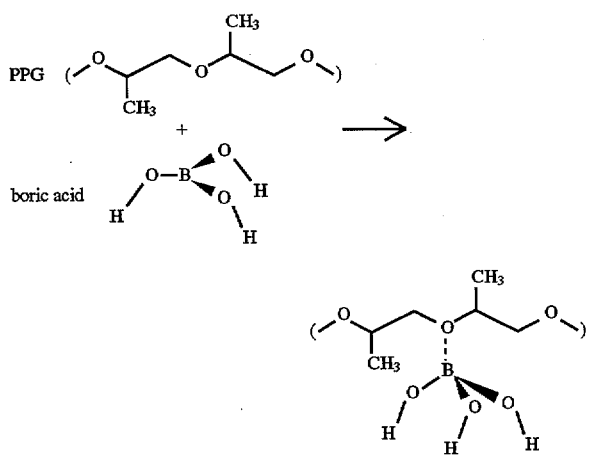

The next element, carbon, usually hybridizes to have 4 electrons singally placed in four hydbrid $sp^3$ orbitals. This leaves no lobes empty for coordinate covalent bonding and electron additions proceeding further across that row of the periodic table also leave no lobes empty. Hence, boron is the only element in the second row of the periodic table that is capable of forming coordinate covalent bonds.

Next the third row begins to fill, and the two 3s electrons fill first in sodium and magnesium. Sodium and magnesium have empty d orbitals available for coordination. Examples of magnesium coordination compounds are common. Then aluminum, like boron, places one electron in one of the 3p lobes, and the two other 3p lobes are empty and available for coordinate covalent bonding. The same trends continue across the third row, but the third row elements also have available five 3d lobes so the potential for coordination bonding exists even though 3p orbitals are occupied in the third row. Hence, Al, P, S, and Cl are capable of accepting a pair of electrons from an electron-pair donor to form a coordinate covalent bond. An example of this is found in the bonding in PCl$_5$, aluminum trihydrate, or phosphorous pentasulfide. A phosphorous pentasulfide particle can be used to increase flammability of a product, while aluminum trihydrate is a fire retardant. An example of a coordinate covalently bonded aluminum compound is

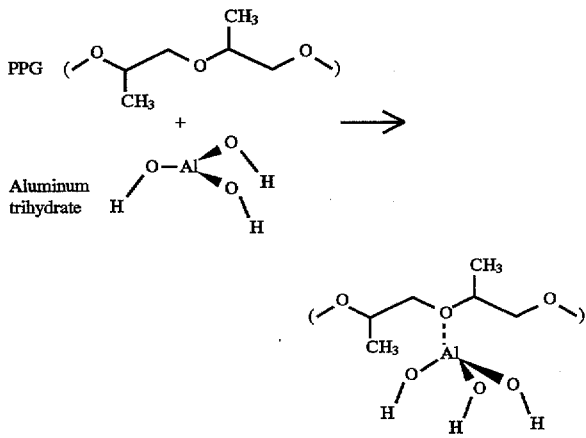

aluminum trihydrate, which may participate in a coordinate covalent bond with a polypropylene glycol (PPG) polymer. In this example, the aluminum atom of aluminum trihydrate acts as an electron acceptor for an electron pair donated by an oxygen atom of a binder according to the present invention. As illustrated above, an oxygen atom of polypropylene glycol (PPG) donates a pair of electrons to aluminum trihydrate, thereby forming a coordinate covalent bond between an aluminum trihydrate particle and a binder, in this case a PPG binder. The same may hold true for the oxygen atoms of the glycerin and glycerin-ester binders of the present invention. The depiction of aluminum trihydrate shown above is not typical of the aqueous chemistry of aluminum, but rather is provided to illustrate the type of bonding that may occur in a coordinate covalent bond.

In the next row, the 4s orbital is filled first, then the 3d lobes begin to fill one electron per lobe until all have added a single then a second electron to each lobe until all lobes are filled. However, 4p and 4f orbitals also are available, hence many of the transition elements are capable of forming coordinate covalent bonds.

The elements that have empty orbitals that participate in coordinate covalent bonding include all those except the metals (which excludes hydrogen) in periods one and two, and C, N, O, F, Ne and He. These metals do not have sufficient affinity for electrons to participate in coordinate covalent bonding. Especially preferred particles contain boron, aluminum, iron, rhodium, osmium, platinum, and palladium, and most particularly boron. Examples of particles that are capable of coordinate covalent bonding are aluminum trihydrate, antimony oxide, arsenic disulfide, bismuth aluminate, bismuth iodide oxide, bismuth phosphate, bismuth subcarbonate, bismuth subgallate, cadmium salycilate, chromic carbonate, chromic hydroxide, chromic oxide, and chromic phosphate. All of the binders of the present invention are capable of donating a lone pair of electrons from an electronegative atom, such as oxygen or nitrogen, to form a coordinate covalent bond with a suitable particle that includes an atom having an empty orbital for accepting electrons to form a coordinate covalent bond.

IV. Superabsorbent Particles

In one disclosed embodiment the added particles are superabsorbent particles, which comprise polymers that swell on exposure to water and form a hydrated gel (hydrogel) by absorbing large amounts of water. Superabsorbents are defined herein as materials that exhibit the ability to absorb large quantities of liquid, i.e., in excess of 10 to 15 parts of liquid per part thereof. These superabsorbent materials generally fall into three classes, namely starch graft copolymers, crosslinked carboxymethylcellulose derivatives and modified hydrophilic polyacrylates. Examples of such absorbent polymers are hydrolyzed starch-acrylonitrile graft copolymer, a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-crosslinking polyacrylic acid, a crosslinked polyacrylate salt, carboxylated cellulose, and a neutralized crosslinked isobutylene-maleic anhydride copolymer.

Superabsorbent particles are available commercially, for example starch graft polyacrylate hydrogel fines (IM 1000F) from Hoechst-Celanese of Portsmouth, Va., or larger particles such as granules. Other superabsorbent particles are marketed under the trademarks SANWET (supplied by Sanyo Kasei Kogyo Kabushiki Kaisha), SUMIKA GEL (supplied by Sumitomo Kagaku Kabushiki Kaisha and which is emulsion polymerized and spherical as opposed to solution polymerized ground particles), FAVOR (supplied by Stockhausen of Greensboro, N.C.), and NORSOCRYL (supplied by Atochem). The superabsorbent particles come in a variety of sizes and morphologies, for example IM 1000 and IM 1000F. The 1000F is finer and will pass through a 200 mesh screen whereas IM 1000 has some particles that will not pass through a 60 mesh screen. Another type of superabsorbent particle is IM 5600 (agglomerated fines). Superabsorbent particulate hydrophilic polymers also are described in detail in U.S. Pat. No. 4,102,340. That patent discloses hydrocolloid absorbent materials such as cross-linked polyacrylamides.

V. Other Particles

Many particles that form hydrogen bonds or coordinate covalent bonds are suitable for use with the present invention. Some such particles are listed in Table I with an indication of the function of the listed particles. The particles listed in Table I are water-insoluble particles.

TABLE I

Water-Insoluble Particulates For Binding

| Name | Function |
| --- | --- |
| Aluminum Trihydrate | Fire retardant, astringent |
| Acediasulfone | Antibacterial |
| Agaricic acid | Antiperspirant |
| Alclometastone | Topical anti-inflammatory |
| Calcium alginate | Topical hemostatic |
| Amidomycin | Fungicide |
| Antimony oxide | Fire retardant |
| Apigenin | Yellow dye, mordant |
| Arsenic disulfide | Red Pigment |
| Aspirin | Anti-inflammatory; antipyretic |
| Azanidazole | Antiprotozoal (Trichomonas) |
| Azelaic acid | Antiacne |
| Baicalein | Astringent |
| Bendazac | Anti-inflammatory |
| Benomyl | Fungicide; ascaricide |
| Benzestrol | Estrogen |
| Benzylpenicillinic acid | Antibacterial |
| Benzylsulfamide | Antibacterial |
| Bergaptene | Antipsoriatic |
| Betasine | Iodine source |
| Bezitramide | Narcotic analgesic |
| Bibrocathol | Topical antiseptic |
| Bietanautine | Antihistaminic |
| Bifenox | Herbicide |
| Bifonazole | Antifungal |
| Binapacryl | Fungicide, miticide |
| Bis(p-chlorophenoxy)methane | Miticide |
| Bismuth aluminate | Antacid |
| Bismuth iodide oxide | Anti-infective |
| Bismuth phosphate | Antacid; protectant |
| Bismuth subcarbonate | Topical protectant |
| Bismuth subgallate | Astringent, antacid; protectant |
| Bisphenol A | Fungicide |
| Bitertanol | Agricultural fungicide |
| Bithionol | Topical anti-infective |
| Bromacil | Herbicide |
| Bromadiolone | Rodenticide |
| Bromcresol green | Indicator |
| Bromcresol purple | Indicator |
| Bromethalinlin | Rodenticide |
| p-Bromoacetanilide | Analgesic; antipyretic |
| 3-Bromo-d-camphor | Topical counterirritant |
| Bromophos | Insecticide |
| Bromopropylate | Acaricide |
| 5-Bromosalicyl-hydroxamic acid | antibacterial (tuberculostatic) |
| 5-Bromosalycilic acid acetate | Analgesic |
| Bromosaligenin | Anti-inflammatory |
| Bromthymol blue | Indicator |

TABLE I-continued

Water-Insoluble Particulates For Binding

| Name | Function |
| --- | --- |
| Broxyquinoline | Antiseptic; disinfectant |
| Bucetin | Analgesic |
| Bumadizon | Analgesic; anti-inflammatory; antipyretic |
| Bupirimate | Fungicide |
| Busulfan | Carcinogen, insect sterilant, antineoplastic |
| Butamben | Topical anesthetic |
| Butrylin | Insecticide |
| Butylated hydroxy-anisole | Antioxidant (BHA) |
| Butyl parabon | Pharmaceutic aid; food preservative |
| 4-tert-Butylphenyl salicylate | Light absorber |
| Cacotheline | Indicator |
| Cactinomycin | Antineoplastic |
| Cadmium salycilate | Antiseptic |
| Calamine | Skin protectant |
| Calcium carbonate | Antacid |
| Calcium saccharate | Pharmaceutic aid |
| Calcium tartrate | Preservative; deodorant; antacid |
| Cambendazole | Anthelminthic |
| Candicidin | Topical antifungal |
| Candidin | Topical antifungal |
| Capsaicin | Topical analgesic |
| Captan | Fungicide; bacteriostat |
| Carbadox | Antimicrobial |
| Carbamazepine | Anticonvulsant; analgesic |
| Carbarsone | Antiamebic |
| Carbaryl | Contact insecticide |
| Carbazochrome salycilate | Antihemorrhagic |
| Carbendazim | Fungicide |
| Carbochloral | Hypnotic |
| Carbophenothion | Miticide; insecticide |
| Carboquone | Antineoplastic |
| Carisoprodol | Skeletal muscle relaxant |
| Carthamin | Dye |
| Carvacrol | Disinfectant |
| Cephalin | Local hemostatic |
| Chalcomycin | Antibiotic |
| Chartreusin | Antibiotic |
| Chitin | Vulnerary |
| Chloramben | Herbicide |
| Chloramphenacol palmitate | Antimicrobial |
| Chloranil | Fungicide |
| Chlorbetamide | Antiamebic |
| Chlordimeform | Insecticide |
| Chlorfenac | Herbicide |
| Chlorfenethol | Acaricide |
| Chlorhexidine | Topical antibacterial |
| Chloroazodin | Antibacterial; topical anesthetic |
| Chlorophacinone | Anticoagulant rodenticide |
| p-Chlorophenol | Antiseptic |
| Chlorothricin | Antibiotic |
| Chlorotrianisene | Estrogen |
| Chloroxylenol | Antiseptic; germicide |
| Chlorphenesin | Topical antifungal |
| Chlorphenesin carbamate | Relaxant (skeletal muscle) |
| Chlorphenoxamide | Antiamebic |
| Chlorpropamide | Antidiabetic |
| Chlorpyrifos | Insecticide |
| Chlorquinaldol | Topical antibacterial |
| Chlorsulfuron | Herbicide |
| Chlorothion | Insecticide |
| Chlozoxazone | Relaxant |
| Cholesterol | Pharmaceutic aid |
| Chromic carbonate | Pigment |
| Chromic hydroxide | Pigment |
| Chromic oxide | Abrasive |
| Chromic phosphate | Green pigment |

TABLE I-continued

Water-Insoluble Particulates For Binding

| Name | Function |
|---|---|
| Chrysamminic acid | Explosive |
| Chrysarobin | Antipsoriatic |
| Cilastazol | Antithrombotic |
| Cinoxate | Sunscreen agent |

Other suitable water-insoluble particles include proteins, vitamins, zeolites and silica, each of which contains electronegative atoms, such as oxygen or nitrogen groups, or both. An example of a suitable zeolite is Abscents odor absorber available from UOP of Tarrytown, N.Y. An example of a suitable antimicrobial particle is chlorhexidine (N,N"-Bis(4-chlorophenyl)-3,12-diimino-2,4,11,13-tetraazatetradecanediimidamide). The list in Table I is by no means exhaustive as it can be readily determined for each type of particle whether it is capable of forming a hydrogen bond or a coordinate covalent bond. Many of the particles are non-absorbent, or not superabsorbent polymers.

The particles listed in Table I have chemical properties that make them suitable for binding to fibers with the binders of the present invention. The listed particles are organic or inorganic compounds that have little or no water solubility, yet have the capacity to hydrogen bond or coordinate covalent bond. Water solubility is preferably low, for example, less than 10 g dissolves completely in 300 ml of water at 25° C., more preferably less than about 1 g in 300 ml at 25° C. This low solubility allows the particles to remain solid, and the hydrogen-bonding or coordinate covalent bonding capacity allows them to adhere to the fibers even in cases when an aqueous binder is used. Once bound, the particles substantially retain a discrete particulate form instead of dissolving or fusing. Hence, once bound more of the particles are discrete than agglomerated.

Many water-soluble particles that are capable of forming hydrogen bonds or coordinate covalent bonds are suitable for use with the binders of the present invention. Some such water-soluble particles are listed in Table II with an indication of the function of the listed particles.

TABLE II

Particulates For Binding

| Name | Function |
|---|---|
| Ethylenediaminetetraacetic acid (EDTA) | Odor absorbent |
| disodium salt of EDTA | Chelator |
| Sodium bicarbonate | Odor absorbent/pH modifier |
| Acarbose | Antidiabetic |
| Acefylline Piperazine | Bronchodilator |
| Acenocoumarol, sodium salt | Anticoagulant |
| Acephate | Insecticide |
| Acetaminophen | Analgesic |
| Acetylleucine Monoethanolamine | Antivertigo agent |
| Acid Violet 7B | Dye/Stain |
| Acitretin | Antipsoriatic |
| Acranil | Antiprotozoal (Giardia) |
| Acriflavine | Anti-infective |
| Actaplanins | Growth stimulant |
| Algestone Acetophenide | Antiacne |
| Algin | Hemostatic |
| Almagate | Antacid |
| (−)-Ambroxide | Fragrance |

TABLE II-continued

Particulates For Binding

| Name | Function |
|---|---|
| Ambucaine hydrochloride | Local anesthetic |
| Amodiaquin | Antimalarial |
| Anabasine hydrochloride | Insecticide |
| o-Anisaldehyde | Fragrance |
| Anisomycin hydrochloride | Topical antitrichomonal |
| Aralkoniuim chloride | Antiseptic, germicide |
| Asiaticoside | Dermatide, wounds, burns |
| Aspartame | Non-nutritive sweetener |
| Azidoamphenicol | Antimicrobial in eye infections |
| Bebeerine | Antimalarial |
| Potassium benzoate | Preservative, antifungal |
| Benzoyl peroxide | Dermatide, antiacne |
| Benzylidene acetone | Fragrance |
| Bidrin | Insecticide |
| Biphenamine hydrochloride | Antiseborrheic |
| Bishydroxycoumarin | Anticoagulant |
| Bismuth tribromophenate | Topical antiseptic |
| Blasticidin S hydrochloride | Antimicrobial |
| Bromocresyl green | Indicator |
| Bromophenol blue | Indicator |
| Butathamine hydrochloride | Anesthetic |
| Caffeine hydrochloride | CNS Stimulant |
| Calcium ascorbate | Vitamin C/Calcium source |
| Calcium bisulfite | Germicide |
| Calcium thioglycollate | Depilatory |
| Carbachol | Ophthalmic parasympathomimetic |
| Carbowax | Ointment base |
| Cetalkonium chloride | Antibacterial |
| Cethoxonium bromide | Antiseptic |
| Chartreusin | Antimycobacterial |
| Chloramine-T | Topical antiseptic |
| Cinnamic acid | Fragrance |
| Cotamine chloride | Hemostatic |
| Demercarium bromide | Topical antiglaucoma |
| D-2-deoxyribose | DNA synthesis |
| Dequalinium chloride | Antiseptic |
| Dermostatin | Anti fungal |
| Dexamethasone | Glucocorticoid |
| Diacetone acrylamide | Mfr coatings, adhesives |
| 2,4-Diamino-6-hydroxypyrimidine | Indicator of nitrates/nitrites |
| 2,4-Diaminophenol dihydrochloride | Photographic developer |
| Diamthazole dihydrochloride | Antifungal |
| Diatrizoate sodium | Diagnostic aid |
| Dibekacin sulfate | Antibacterial |
| Disodium 4',5'-dibromofluorescein | FDA approved dye |
| 3,5-Dibromo-4-hydroxybenzensulfonic acid, sodium salt | Topical disinfectant |
| Dibromopropamidine | Cosmetic preservative |
| Diflorasone | Topical anti-inflammatory |
| Dihydroxyacetone | Artificial tanning agent |
| Diisobutyl sodium sulfosuccinate | Wetting agent/detergent |
| Dikegulac | Plant growth regulator |
| Dimethisoquin | Topical anesthetic |
| Diphenicillin sodium | Antibacterial |
| Diphetarsone | Antiamebic |
| Dipyrone | Analgesic, antipyretic |
| Diquat dibromide | Herbicide, defoliant |
| Dodine | Fungicide |
| Domiphen bromide | Topical anti-infective |
| Dulcin | Non-nutritive sweetener |
| Dymixal ® | Topical burn treatment |
| Ecognidine | Topical anesthetic |
| Edetic acid | Antioxidant |
| Edoxudine | Antiviral |
| Ellagic acid | Hemostatic |
| Endothal | Herbicide, defoliant |
| Eosine I bluish | Dye |
| Eosine yellowish | Cosmetic dye |

TABLE II-continued

Particulates For Binding

| Name | Function |
| --- | --- |
| Erythrosine | Food dye |
| Esculin | Skin protectant |
| Ethacridine | Antiseptic |
| Ethambutol hydrochloride | Antibacterial (tuberculostatic) |
| Ethamsylate | Hemostatic |
| Ethylidene dicoumarol | Anticoagulant |
| Ethylstibamine | Antiprotozoal |
| Euprocin dihydrochloride | Topical anesthetic |
| Fast green FCF | Food coloring |
| Fenticonazole nitrate | Topical antifungal |
| Ferric albuminate | Hematinic |
| Ferric chloride hexahydrate | Astringent, styptic |
| Ferric formate | Silage preservative |
| Ferulic acid, sodium salt | Food preservative |
| Fluorescein, disodium salt | Diagnostic aid |
| Fluoridamid | Plant growth retardant |
| Forminitrazol | Antiprotozoal (Trichomonas) |
| Fortimicin(s) | Antibacterial |
| Foscarnet sodium | Antiviral (HIV-1) |
| Fosetyl Al | Systemic fungicide |
| Fungichromin | Topical antifungal |
| Gallic acid | Astringent, styptic |
| Gentian violet | Topical anti-infective |
| Gluconolactone | Cleaner |
| Gossypol | Rubber antioxidant |
| Heparin | Anticoagulant |
| Hexamethylolmelamine | Fireproofing agent |
| Mexamidine | Antiseptic, anti-acne |
| Homatropine | Anticholinergic (opthtalmic) |
| Hydrastinine hydrochloride | Uterine hemostatic |
| Hydrocortisone phosphate, disodium salt | Glucocorticoid |
| Hydroquinine hydrochloride hemihydrate | Depigmentor |
| Hydroxyamphetamine hydrobromide | Andregenic (opthtalmic) |
| Hydroxybutyranilide | Antioxidant |
| 3-Hydroxycamphor | Topical antipruritic |
| 1-(Hydroxymethyl)-5,5-dimethylhydantion | Cosmetic preservative |
| 8-Hydroxyquinoline sulfate | Antiperspirant, deodorant |
| Iodic acid | Astringent |
| Itraconazole | Antifungal |
| Kanamycin(s) | Antibacterial |
| Kermesic acid | Dye |
| Kojic acid | Flavor enhancer |
| Laccaic acid | Crimson dye |
| Lactic acid | Acidulant |
| Litimus | Indicator |
| L-Lysine L-glutamate | Flavor additive |
| Lyxoflavine | Feedstuff, growth-promoter |
| Maclurin | Dye |
| Malachite green | Dye |
| Maltol | Flavor enhancer |
| Maneb | Agricultural fungicide |
| Manganese acetate | Mordant |
| Meralein sodium | Topical anti-infective |
| Plus a host of others, including a wide range of inorganic salts. | |

The list in Table II is by no means exhaustive as it can be readily determined for each type of particle whether it is capable of forming a hydrogen bond or a coordinate covalent bond. All or most of the particles are non-absorbent, or not superabsorbent polymers. Solubility of the particle in water and the binder can be easily ascertained, for example in standard chemical reference materials.

The particles listed in Table II have chemical properties that make them suitable for binding to fibers with the binders of the present invention. The listed particles are organic or inorganic compounds that are water soluble, yet have the capacity to hydrogen bond or coordinate covalent. Water solubility is preferably high. By water soluble it is meant that more than about 10 g of the particles will dissolve in 300 ml of water at 25° C. The range of solubilities can extend, for example, from a lower limit of 10 g in 300 ml of water at 25° C., to an upper limit in which the particle is miscible in all proportions with water at 25° C. This high solubility allows the particles to dissolve when exposed to aqueous liquids such as urine, but the hydrogen-bonding or coordinate covalent bonding capacity allows them to adhere to the fibers in the presence of binder but in the absence of aqueous liquid during use by an end user after the manufacturing process is completed. While bound, the particles substantially retain a discrete particulate form instead of dissolving or fusing, at least until they are exposed to an aqueous liquid. More of the particles are discrete rather than agglomerated while bound in the absence of an aqueous liquid. If the particles are exposed to fibers with binder in liquid form, for the particles to retain their particulate form, a binder is preferably selected so that the particles are sparingly soluble in the binder. By sparingly soluble it is meant that no more than about 5 g of particles dissolve in 300 ml of the binder at 25° C.

The amount of particles added to the fibers can vary widely, for example from 0.05 to 80 percent of the total weight of the fibrous material and particles. Antimicrobials, such as chlorhexidine or other nonabsorbent particles, are effective in very low amounts, such as 0.05 to 10 percent. Superabsorbent particles are preferably added in an amount of 3–60 percent, especially 20–60 percent by weight of the fibrous materials and particles. The particles may be combined to include more than one type of particle, for example superabsorbent and nonsuperabsorbent particles, or two types of superabsorbent particles. When two types of particles are used, the total weight of the particles will not exceed 80 percent of the total weight of the fibrous material and particles.

VI. Binder Characteristics

The particles may be bound to the fibers by an organic binder, which may be water soluble. The binder typically comprises binder molecules, and the binder is selected from a predetermined group of binders, wherein the binder molecules have at least one hydrogen bonding functionality and at least one hydrogen bonding or coordinate covalent bond forming functionality. In accordance with the present invention, the predetermined group of binders may include binder molecules having a functional group selected, without limitation, from the group consisting of a hydroxyl, a carboxyl, a carboxylate, a carbonyl, an amide, and combinations thereof, wherein each binder includes at least two such functionalities, and the two functionalities are the same or different.

The vapor pressure of the binder may, for example, be less than 10 mm Hg at 25° C., and more preferably less than 1 mm Hg at 25° C. The binder molecule has at least one functional group that forms hydrogen bonds or coordinate covalent bonds with the particles, and at least one functional group that forms hydrogen bonds with the fibers. In accordance with the present invention, the predetermined group of binders may include, without limitation, a functional group selected from the group consisting of a carboxyl, a carboxylate, a carbonyl, a sulfonic acid, a sulfonate, a phosphate, a phosphoric acid, a hydroxyl, an amide, an amino, and combinations thereof (such as an amino acid or hydroxy acid) wherein each binder includes at least two such functionalities, and the two functionalities are the same or different. As used herein, the term "binder" refers to a monomer, dimer, trimer, tetramer, and oligomers, although some particular binders are monomeric and dimeric, preferably monomeric.

Particularly preferred binders are capable of forming five or six membered rings with a functional group on the surface of the particle. A six-membered ring also is formed by hydroxyl groups, such as may be found with alcohols, for example, as shown below:

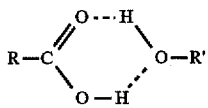

A five membered ring can be formed by the binder and the functionality on the surface of the particle, for example:

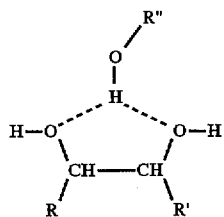

wherein the particle is a water-insoluble particle such as SAP and the binder is an alcohol or polyol, with hydroxyl groups on adjacent carbons, for example glycerin. A binder that forms a five-membered ring can also be used with a water-soluble particle, for example wherein the particle is EDTA and the binder is an alcohol, such as a polyol with hydroxyl groups on adjacent carbons, for example glycerin.

Other alcohols that do not form a five-membered ring also can be used, for example alcohols that do not have hydroxyl groups on adjacent carbons. Examples of suitable alcohols include primary, secondary or tertiary alcohols.

A polyol is an alcohol that contains a plurality of hydroxyl groups, and includes triols such as glycerin (1,2,3-propanetriol); esters of hydroxyl containing binders also may be used with mono- and diesters of glycerin as examples. The mono- and diesters as referred to herein include monoglycerides and diglycerides.

Non-polymeric polyamide binders are small molecules (for example, monomers or dimers) that have more than one amide group, such as oxamide, urea and biuret.

Although other binders are suitable, the binder preferably is selected from the group consisting of glycerin, a glycerin monoester, a glycerin diester, a propylene glycol, a propylene glycol oligomer, a polyglycerin oligomer, urea, and combinations thereof. As used herein, an oligomer refers to a condensation product of polyols, wherein the condensation product contains less than ten monomer units. A polyglycerin oligomer as referred to herein means a condensation product of two or more glycerin molecules. A propylene glycol oligomer as referred to herein means a condensation product of two or more propylene glycol molecules. The binder also may be selected from the group consisting of glycerin, a glycerin monoester, a glycerin diester, a propylene glycol, a propylene glycol oligomer, and a polyglycerin oligomer. The binder also may be selected from the group consisting of glycerin, urea, and combinations thereof, or may be selected from the group consisting of a glycerin monoester and a monoglyceride, or a glycerin diester or a diglyceride. Presently, the binder preferably is glycerin or glycerin and urea. When urea and glycerin are combined, they may be combined, based on the total weight of the binder, from about 40 weight percent to about 100 weight-percent glycerin, more preferably from about 50 to about 90 weight-percent glycerin, and even more preferably from about 45 to about 70-weight-percent glycerin.

Each of the binders disclosed above comprise binder molecules, wherein the binder molecules are capable of forming hydrogen bonds because the molecules have at least one functional group that contains electronegative atoms, particularly oxygens or nitrogens, or has electronegative groups, particularly groups containing oxygens or nitrogens, and that also include a hydrogen. The glycerin, glycerin monoester and glycerin diester binders all have a hydroxyl group in which a hydrogen is bound to an electronegative oxygen, creating a dipole that leaves the hydrogen partially positively charged. Amide binders, such as urea, have an $NR_2$ group in which a hydrogen may be bound to an electronegative nitrogen that also leaves the hydrogen partially positively charged. The partially positively charged hydrogen in such cases then can interact with an electronegative element, such as oxygen or nitrogen, on the particle or fiber to help adhere the binder to the particle and fiber. Similarly, electronegative atoms (such as oxygen or nitrogen) on the fiber or particle can interact with hydrogen atoms on the binder that have positive dipoles, and partially positive hydrogen atoms on the fiber or particle can interact with electronegative atoms on the binder.

Several proposed hydrogen bonding interactions of two binders (glycine and 1,3-propanediol) with cellulose are shown below:

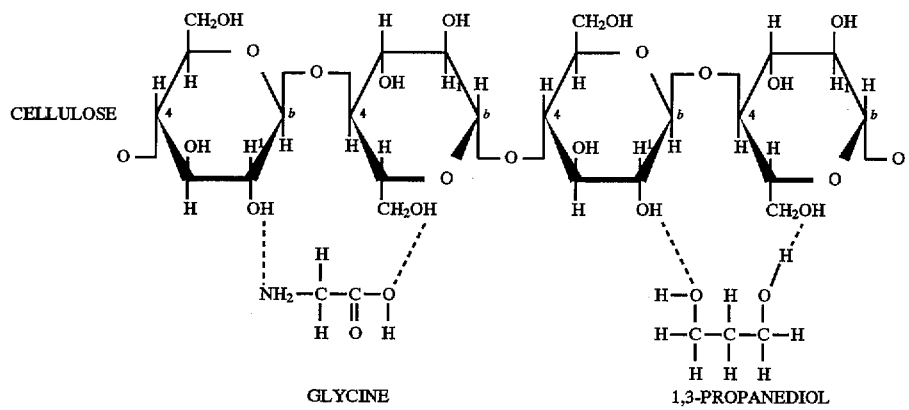

The hydrogen bonding interactions are shown as dotted lines. One such interaction is shown between the nitrogen of glycine and a hydrogen of an —OH on cellulose. A hydrogen bond with glycine is also shown between an oxygen of the —OH on glycine and the hydroxy hydrogen of an alcohol sidechain on cellulose. Hydrogen bonding interactions of the 1,3-propanediol are shown in dotted lines between an oxygen on an —OH group of the binder and a hydrogen of an —OH group on the cellulose molecule. Glycerin, which is 1,2,3-propanetriol, would form hydrogen bonds in a manner similar to that shown for 1,3-propanediol. However, glycerol contains an additional hydroxy group, that is capable of many other hydrogen bonding interactions as shown for 1,3-propane-diol. Another hydrogen bond is also shown between a hydrogen on an —OH group of the glycol binder and an oxygen in an alcohol sidechain of the cellulose.

Hydrogen bonding interactions are shown as dotted lines. One such interaction is shown between the nitrogen of glycine and a hydrogen atom of an —OH on cellulose. Similar bonds can be expected to form at the NH$_2$ groups of urea.

It also is possible for water or other hydrogen-bonding molecules to be interposed between the fiber and binder, such that the fiber and binder are both hydrogen bonded to the water molecule.

Alternatively, an atom on the binder may have an unshared pair of electrons, such as a lone pair of electrons from an oxygen or nitrogen atom, that can be donated to an empty orbital of an acceptor atom in the particle to form a coordinate covalent bond. The unshared pair of electrons on the oxygen or nitrogen can be donated to an empty p, d or f orbital of a particle (for example a boron-containing particle) to form a coordinate covalent bond that adheres the particle to the binder. The fibers themselves do not normally contain functional groups that can act as electron acceptors in the formation of coordinate covalent bonds with the binders, but hydrogen bonding interactions allow the binder to adhere to the fiber. Cellulosic and synthetic fibers, for example, contain hydroxyl, carboxyl and ester groups that will hydrogen bond with the hydroxyl, carboxylic acid, amide, amine or other groups of the binder. Non-cellulosic or non-synthetic fibers that have these functionalities also can be used, for example silk, which has an amide linkage. Hence the binder will adhere the particle with a coordinate covalent bond and the fiber with a hydrogen bond.

In some preferred embodiments, the binder is bound to both the fibers and the particle by hydrogen bonds. A polyol binder, glycerin for example, can be used to bind polyacrylate hydrogel particles to cellulosic fibers. The hydroxyl groups on the polyol binder participate in hydrogen-bonding interactions with the hydroxyl groups on the cellulose fibers and the carboxyl groups on the polyacrylate hydrogel. Hence, the binder will adhere to both the particle and fiber with hydrogen bonds. These hydrogen bonds provide excellent binding efficiency and diminish separation of bound particles from the fibers.

A structural drawing is shown below in which citric acid, vitamin C and urea adhere water-insoluble SAP particles to cellulose with hydrogen bonds, or water-soluble EDTA particles. Some of the possible hydrogen bonding interactions are shown as dashed lines. It is possible that other molecules (such as water molecules) also may participate in some of these bonds, for example, as an intermediary between the binder and particle or fiber.

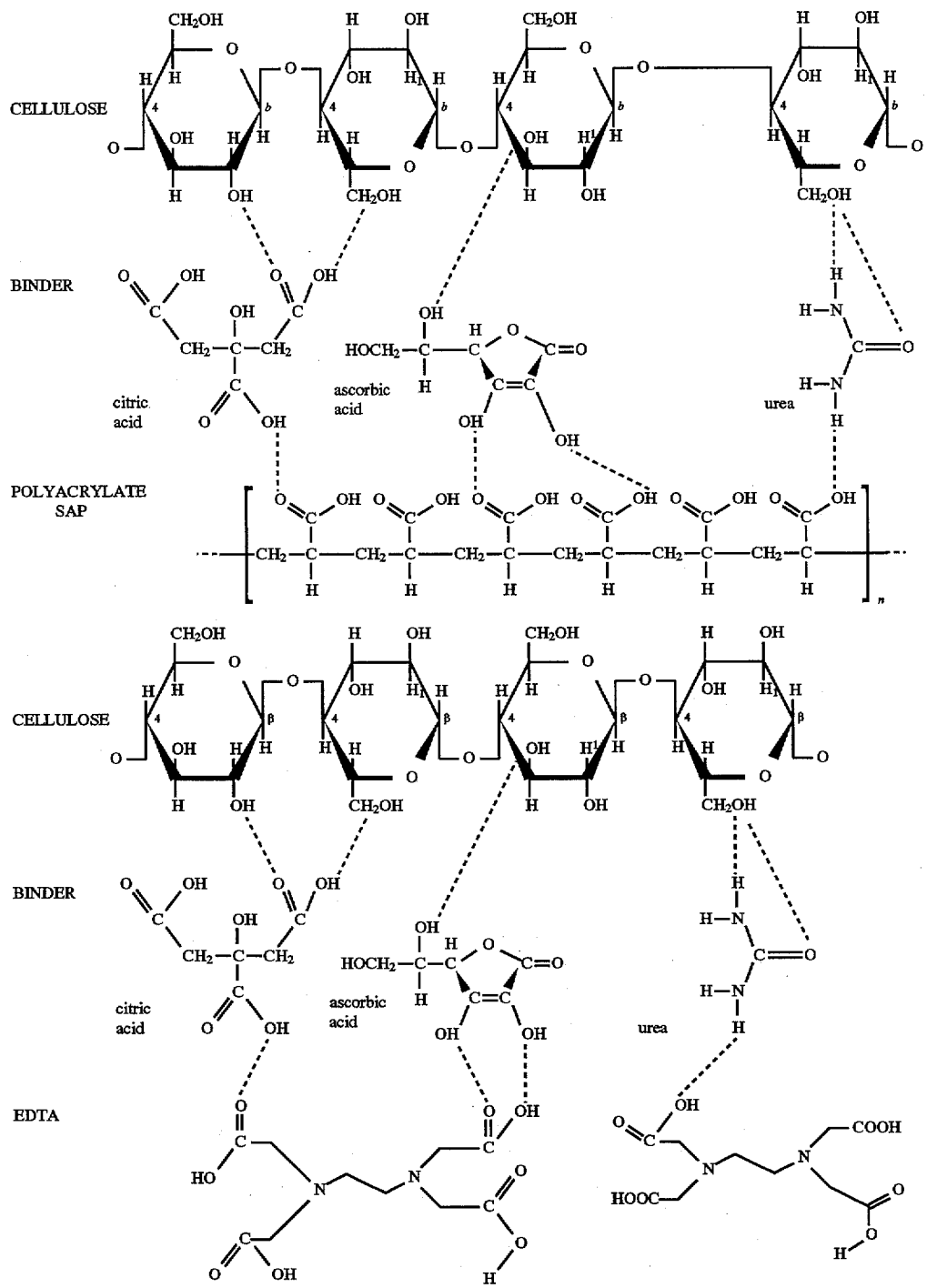

Particularly efficient hydrogen bonding binders include those with carboxyl groups, such as ascorbic acid, or amide groups, such as urea. Hydroxyl groups are also very efficient binders. Amine and ether functionalities are less efficient binders.

Binders have functional groups that may be selected, without limitation, independently or in combination from the group consisting of a carboxyl, a carboxylate, a carbonyl, a hydroxyl, a sulfonic acid, a sulfonate, a phosphoric acid, a phosphate, an amide, an amino, and combinations thereof. These functional groups might be provided by the following exemplary chemical compounds: a carboxyl group could be provided by carboxylic acids, such as ascorbic acid; a carboxylate, which is an ionized carboxylic acid, could be provided by a material such as ascorbate; a carbonyl group can be provided by an aldehyde, such as ketone; a hydroxyl, such as an alcohol or a polyol, such as glycerol, or a mono- or diglyceride, which are esters of glycerol; an amide, such as a peptide; and an amino, which may be provided by an alkyl amine, such as ethylenimine wherein the binder has at least two of these functional groups, and each of the functional groups can be the same (for example, a polyol, polyaldehyde, polycarboxylic acid, polyamine or polyamide) or different (for example, an amino alcohol, hydroxyamide, carboxyamide, or amino acid). Functional groups also may be selected independently or in combination from the group consisting of carboxyl, an alcohol, an amide and an amino. An aldehyde may optionally be a member of each of these groups, particularly if it is oxidized to a carboxylic acid.

Combinations of the binders, as well as with other binders, also may be used, providing that they are non-reactive. That is, providing that the binders do not react in a manner which prevents the binders from possessing the functional groups required to be present for binding in accordance with the present invention.

VII. Process Advantages

The binders of the present invention also provide numerous process advantages. Binding of particles to the fibers can occur, for example, without external application of heat. Hence, if desired, particle binding may occur at ambient temperature. The present invention therefore is distinct from prior-art crosslinking processes in which elevated temperatures are required to covalently crosslink cellulose groups to one another. Moreover, the binders of the present invention have the advantage of being activatable by addition of a fluid, such as a liquid solvent (sometimes referred to herein as an activation liquid, one example of which is water). Hence, a liquid binder (which would include a solution of a solid or liquid binder, or a binder that has a melting point below room temperature) can be applied to a cellulose mat in the absence of the particles to be bound and the binder allowed to dry, for example until the fiber product reaches an equilibrium moisture content with the moisture in the ambient air. The binders then may be activated to bind the particles in place. Some of the binders (especially the liquid binders) diffuse throughout the fibers to reach an equilibrium distribution of the binder.

Alternatively, the binder can be applied as a solid, for example as particles or a powder. At a later stage of processing, water or another activating fluid or liquid may be added to those portions of the mat where particulate binding is desired. The particles then may be added to the mat and adhered to those portions of the mat that have been activated. Alternatively, the particles may be added to the mat prior to or simultaneously with activation of the binder.

The binders may be liquids at room temperature (such as glycerin), or liquid solutions of binders that are solids at room temperature, or liquid hot melts of solid binders. Solid binders may be added to fibers in particulate form, for example, by sprinkling binder particles on the fibers, provided they are fixed by the subsequent application of heat or liquid.

The binding reaction of the present invention can occur across a broad range of pH without requiring a catalyst. A suitable pH range without a catalyst is 1–14, but preferred ranges are 5–8 or 6–8 because such neutral pH ranges will produce fibrous products (such as cellulose products) that are less prone to damage by acid hydrolysis. A non-acidic pH (7 or greater) will provide an environment that inhibits formation of ester bonds, and promotes formation of the hydrogen bonds or coordinate covalent bonds that adhere the particles of the present invention to the fibers with the binder.

When water-insoluble particles are used, the moisture content of the fibers during the binding reaction is 0.5–50%, suitably 5–40%, or preferably 5–20% water by weight of the fibers, binder and particle. A moisture content greater than 20%, preferably 30%, or in the range 20–50%, or 30–50%, can be used even though such high moisture contents interfere with intermediate formation and inhibits formation of covalent bonds in the production of high-bulk crosslinked fibers. When water-soluble particles are used, the moisture content of the fibers during the binding reaction is 0.5–30%, suitably 5–25%, preferably 12–20%. Particles may be added to the fibers with the particles distributed throughout a fibrous product without being confined to a surface of the product. The particles can be distributed throughout the depth of a fiber product such as a mat or web.

The binder suitably is present in the treated product in an amount of at least 0.0 percent, and no more than 80 percent, by weight of the fibrous material ("percent by weight"). In especially preferred embodiments, the binder is present in an amount of 1–80, or more preferably, 1 to 40 or 1 to 25 percent by weight of the fibrous material. Below about 1 percent, when placed on the fiber, an insufficient amount of binder is present to achieve adequate binding. Using excessive amounts of binder can introduce unnecessary expense into the binding process. High percentages of binder can also cause processing problems because the binder material transfers to equipment surfaces. Therefore, it is often preferred to use no more binder than is required to bind the particles and fibers.

Thermoplastic or meltable binders also may be used to help bind fibers to each other and particles to fibers. The binder that has the hydrogen bonding or coordinate covalent bonding functionalities itself may be thermoplastic or meltable. Hence, fibers treated in accordance with the present invention can be thermobonded by elevating the fiber temperature above the melting or softening temperature of the binder to melt or soften the thermoplastic or meltable binder and physically bind the fibers to each other or the fibers to the particles. Alternatively, an auxiliary or second binder can be applied to the fibers as a solid at room temperature, and the temperature of the second binder elevated above its melting or softening point to thermobond the fibers and particles. The auxiliary binder may be applied to the fibers either before or after the primary binder is applied, but before thermobonding.

The binders of the present invention may be used with fibers that have substantial intrafiber covalent crosslinks (such as HBA pulp available from Weyerhaeuser) or fibers which are substantially free of intrafiber covalent crosslinking. Examples of individualized intrafiber crosslinked fibers are seen in European Patent Applications 440 472 A1 and 427 317 A2, which produce products that those publications describe as being substantially free of interfiber bonds. The fibers of the present invention do not need to be processed as in those European applications to eliminate interfiber bonds. Binders of the present invention can therefore be used with natural fibers that have substantial interfiber bonding, which are defined as fibers that have not been processed as in European Applications 440 472 A1 and 427 317 A2 to substantially eliminate interfiber bonds. Cellulose fibers that have not been so processed are substantially free of intrafiber bonds.

The fibrous product of the present method (with or without intrafiber crosslinking) may further be densified by external application of pressure. The densified product is compact and easily transported. And, when the particles are superabsorbent particles, the resulting fibrous product has superior properties as compared to nondensified products. The inventors have found that the binders of the present invention produce a product that can be easily densified.

Easy densification is associated with the hydrogen bonds and coordinate covalent bonds formed between the binder and the particles and fibers. The fibers are particularly easily densified when at least 5% by weight of the fibers, particles and binder, more preferably at least 10%, are SAP particles adhered to the fibers.

In accordance with this invention, the binders may be applied to fibers before, subsequent, or simultaneously with addition of the particles. Simultaneous addition can be accomplished by two separate streams of particles and binder that are simultaneously directed at a fibrous substrate, or alternatively merged immediately or some time prior to impacting against the substrate. Without limiting the invention, it appears that the addition of small amounts of moisture to the particles may help bind superabsorbent particles and perhaps other types of particles to the fibers.

Binding may be performed under conditions that favor formation of hydrogen bonds or coordinate covalent bonds, and discourage formation of covalent bonds. Conditions that favor covalent bonds are those disclosed in U.S. Pat. No. 4,412,036 and U.S. Pat. No. 4,467,012 wherein particle and binder would be laminated between tissue layers under high temperature and pressure to form laminated adherent tissue layers. That patent teaches that minimal adhesion occurs at 200 pli (pounds per linear inch, as in a calendar press) if no external heat is supplied, but adhesion improves as the reaction temperature increases. Improved adhesion of the tissue layers occurs because of enhanced covalent bonding as the temperature increases.

Conditions that favor covalent bond formation are also shown in European Patent Applications 440 472 A1; 427 17 A2; 427 316 A2; and 429 112 A2. These European publications use polycarboxylic acid crosslinkers, and require elevated temperatures (for example above 145° C.) and acidic conditions (pH less than 7) to promote formation of intrafiber covalent ester bonds and inhibit reversion of the ester bonds. The present invention, in contrast, can form hydrogen or coordinate covalent bonds below 145° C., below 100° C., and even at room temperature. The binders of the present invention also can bind particles to fibers under neutral or alkaline conditions, i.e., at a pH above 7, but preferably at a pH of 5–8 or 7–8. Fibers that have high bulk from intrafiber covalent crosslinks are prepared by individualizing the fibers (for example, in a fiberizer) and curing them at an elevated temperature (above 150° C.). Initial application of the binder on such high-bulk fibers preferably occurs after the curing step, particularly if the binder is capable of functioning as a crosslinking material, such as dipropylene glycol, which is a polyol. If such binders are present during curing, the binder functionality will be consumed during the curing step to form covalently crosslinked bonds. When this occurs, the binder functionality is no longer available for hydrogen bonding or coordinate covalent bonding, and particle binding to fibers is ineffective.

The intrafiber covalent bond forming processes described in the above European publications require formation of an anhydride that then reacts with a hydroxy group on cellulose to form a covalent ester bond. The presence of more than about 20% water by weight in the fibers is believed to retard the formation of the anhydride and inhibits covalent bond formation. Hence, in processes that use polyols as binders in the present invention, the fibers should contain at least 20% water (or 20–50% water) by weight if the particles and binder are present in the fibers when curing occurs. The water inhibits covalent bond formation, and prevents all of the binder from being used to form covalent intrafiber crosslinks. Hence, some of the binder remains available to form the non-covalent bonds with the particles and produce ease of densification in fiber products made by the process of the present invention.

The present invention, in contrast, produces a product under conditions that favor formation of hydrogen or coordinate covalent bonds. Hence, the particles can be bound to the fibers in the absence of the external application of heat or pressure. Particles also may be bound and the resulting fiber product densified, for example at less than 200 pli (about 8000 psi) with SAP, or preferably less than 100 pli (about 4000 psi) with SAP, in the absence of external application of heat to produce a product in which a substantial portion of the particles are bound by non-covalent bonds (hydrogen or coordinate covalent bonds). A substantial portion of particles bound by non-covalent bonds means at least half of the bonds binding particles to fibers are other than covalent bonds, for example, hydrogen or coordinate covalent bonds.

In yet other examples, particles may be bound in the absence of external application of pressure, but at elevated temperatures.

In particularly preferred embodiments, the particles are substantially entirely bound to the fibers non-covalently.

VIII. Binding Examples

Several examples are provided below to illustrate the use of several binders of the present invention to attach superabsorbent particles to southern bleached kraft pulp. Several examples of binder activation and reactivation also are provided.

EXAMPLE 1

A 3171 gram amount of southern bleached kraft fluff was air-entrained in a blender-like mixing device. While the fluff was air-entrained, 4348 grams of starch graft polyacrylate hydrogel fines (IM 1000F; supplied by Hoechst-Celanese of Portsmouth, Va.) were added to the mixing device and mixed with the fluff. Thereafter, 500 grams of glycerin (96%, USP; supplied by Dow Chemical Co. of Midland, Mich.) diluted with 200 ml of deionized water were sprayed onto the fluff and hydrogel. The material was then shunted into a flash tube dryer at 142° F., blown into a cyclone and fed into a Danweb airlay machine to form a web containing bound 40% IM 1000F that was substantially immobile in the web because the particles were bound to the fibers instead of mechanically entrapped by the matrix.

Glycerin is advantageous because it tends to penetrate the fibers and soften them in addition to binding the particles to the fibers. However, over time less glycerin is available at the surface of the fibers for use in binding particles in the event the glycerin/fiber material is stored for long periods prior to use in adhering particles (e.g. if activation is delayed for several weeks or more). This can be compensated for in part by using higher percentages of glycerin on the fibers. Also, glycerin monoester and glycerin diester binders, which may include monoglycerides and diglycerides, respectively, apparently do not penetrate as readily into the fibers and therefore can be stored longer before activation to adhere particles.

EXAMPLE 2

A 900 gram amount of southern bleached kraft fluff pulp sheet was sprayed with a 50% solution of glycerin (supplied by Dow Chemical, Midland, Mich.) so that the moisture content was 17–21% as the sheet was fed into a Fitz hammermill fitted with a three eighths inch hole screen. Starch graft polyacrylate hydrogel fines (IM 1000F; supplied by Hoechst-Celanese of Portsmouth, Va.) were simultaneously added to the mill by a screw feed device, mixed with the fluff, shunted to an M & J airlay forming machine and airlaid to form a web. The web that resulted contained 20% SAP attached to the fibers substantially uniformly throughout the web without being confined to a surface of the web.

EXAMPLE 3

A 900 gram amount of southern bleached kraft fluff pulp sheet was sprayed with a 50% solution of urea (supplied by J. T. Baker, Phillipsburg, N.J.) so that the moisture content was 17–21% as the sheet was fed into a Fitz hammermill fitted with a three-eighths-inch hole screen. Starch graft polyacrylate hydrogel fines (IM 1000F; supplied by Hoechst-Celanese of Portsmouth, Va.) were simultaneously added to the mill by a screw feed device, mixed with the fluff, shunted to an M & J airlay forming machine and airlaid to form a web. The web that resulted contained 20% SAP attached to the fibers.

EXAMPLE 4

A 900-gram amount of southern bleached kraft fluff pulp sheet was fed into a Fitz hammermill fitted with a three-eighths-inch hole screen. The sheet was defiberized, shunted to an M & J airlay line, and airlaid into a web. As the web emerged, target zones of the web were misted with a 50% solution of glycerin to raise the moisture content to 17–21%. Five gram aliquots of starch graft polyacrylate hydrogel fines (IM 1000F; supplied by Hoechst-Celanese of Portsmouth, Va.) were subsequently sifted onto the target zones. The web that resulted contained target zones with 5 grams of SAP attached to the fibers of each target zone. Portions of the web that were not targeted for lactose application did not adhere the particles well. This is an example of applying the binder to a target zone so that SAP primarily adheres to the target areas where the binder was applied. Target-zone application of SAP can be advantageous because it reduces the cost of the product to provide SAP only in areas of a product where the SAP is needed, for example, the crotch area of a diaper. Placement of SAP in the area where a liquid insult is expected also decreases the necessity for wicking liquid to a SAP impregnated region. This is an advantage because the requirement for wicking can increase liquid leakage in an absorbent product such as a diaper.

EXAMPLE 5

Figure 12:
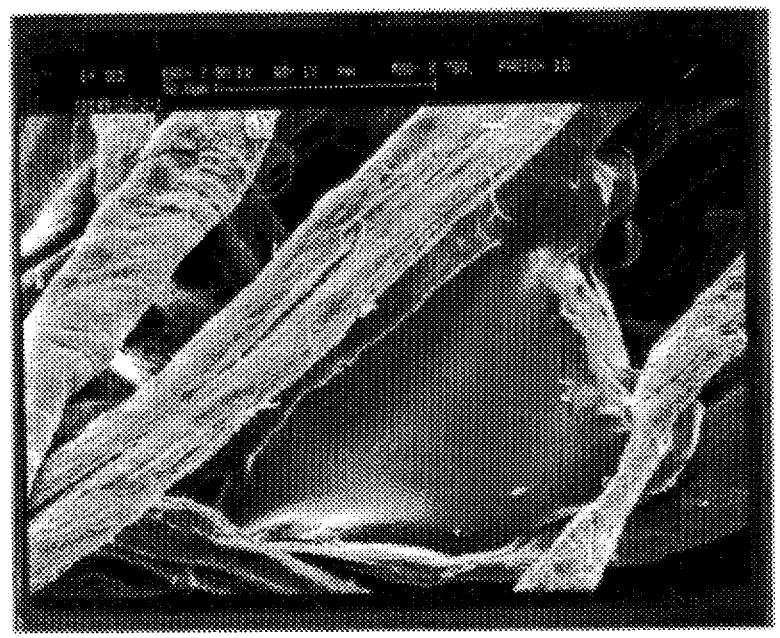
FIG. 12 is a photomicrograph of particles adhered to fibers with urea.

An aqueous solution of 70% urea was prepared by adding 933 grams of urea to 400 milliliters of deionized water. The mixture was heated, with stirring, until the solid urea dissolved, producing a supersaturated solution. A 1200-gram sample of southern bleached kraft pulp sheet was sprayed with the hot solution so that the resulting sheet contained 10% urea. After drying, the sheet was misted with a 25% aqueous solution of glycerin as it entered a hammermill, thereby adding 1% glycerin to the sheet. Simultaneously, a starch graft polyacrylate hydrogel (IM 3900) was added to the mill so that the resulting mixture contained 40% hydrogel based on the weight of the fibers, binders and particles. This mixture was shunted into an M & J airlay machine and airlaid into a web containing 40% bound SAP. Scanning electron microscope (SEM) observation of a sample of that web revealed particles bound to fibers as shown in FIG. 12.

EXAMPLE 6

A glycerin solution containing 40 weight percent urea, based on the total weight of the binder, was prepared by adding 267 grams of urea to 400 grams of glycerin. This mixture was heated, with stirring, until the solid urea dissolved, producing a supersaturated solution. A 1200-gram sample of southern bleached kraft pulp sheet was sprayed with the hot solution so that the resulting sheet contained 4% urea and 6% glycerin. As the sheet was fed into a hammermill, starch graft polyacrylate hydrogel also was added to the hammermill at a rate so that the mixture contained 40% hydrogel based on the weight of the fibers, binders, and particles. The mixture was then airlaid into a web on an M & J airlay machine to produce a web with particles bound to fibers. SEM examination of a sample of that web showed fibers with attached particles as shown in photomicrograph FIG. 13.

The urea/glycerin mixture provides several advantages over the use of glycerin alone. Urea lowers the cost of the binder, while glycerin softens the fibers. The mixture also provides manufacturing advantages.

Urea and urea/glycerin mixtures also may have the advantage of being applied to the fibers so that solid binder remains on the surface of the fibers. Webs made with these fibers can be heated to melt the binder which binds the fibers together to provide improved tensile strength as shown in Table III below.

TABLE III

| Sample | Density (g/cc) | Tensile Index (Nm/g) |
| --- | --- | --- |
| Urea treated fibers (with 40% IM 3900) | 0.1236 | 0.1514 |
| Urea treated fibers (with 40% Im 3900) Thermobonded | 0.1291 | 0.2317 |

In other embodiments urea alone as well as the other binders of the type specified in the foregoing detailed description of the invention and combinations thereof may be used as the binder.

EXAMPLE 7

A 321 gram amount of southern bleached kraft fluff was air-entrained in a blender-like mixing device and 100 grams of glycerin (96%, USP; supplied by Dow of Midland, Mich.) diluted with 30 ml of deionized water were sprayed onto the fluff. 71 grams of Abscents (an odor absorbing zeolite supplied by UOP of Tarrytown, N.Y.) was then added and mixed in the mixing device with the fibers and glycerin for 15 seconds until a homogenous mixture was achieved. The material was then spread out in a fume hood overnight to dry, airlaid into a web and tested for particulate retention by an ash test. The pad so produced contained 7% particulate. The original addition amount should have produced 15%, hence 50% particle retention was observed. This compares favorably to particulate retention with latex binders under similar conditions in which only about 3% of particles are retained.

IX. Binding Examples for Water-Soluble Particles

Several examples are provided below to illustrate using binders of the present invention to attach water-soluble particles to southern bleached kraft pulp.

EXAMPLE 8

Figure 16:
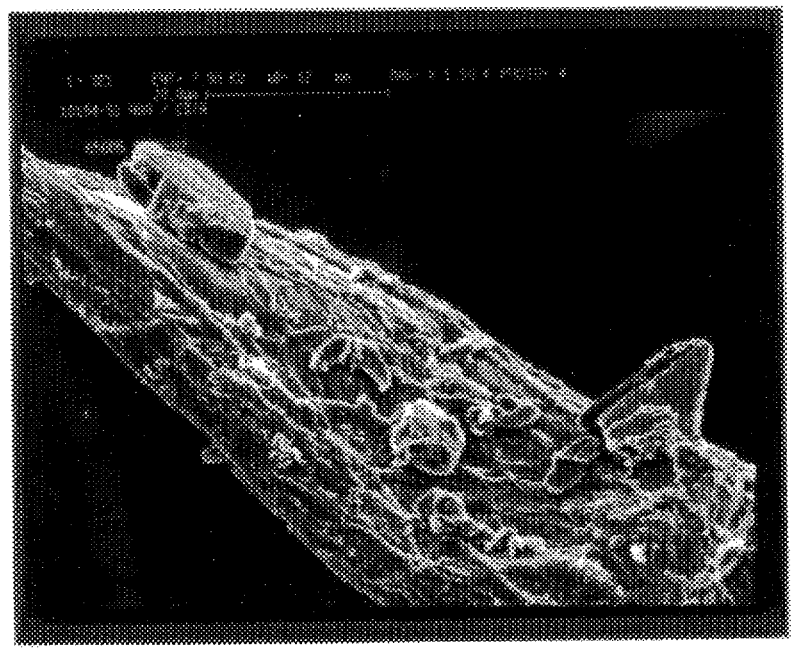
FIG. 16 is a photomicrograph of ethylenediaminetetraacetic acid (EDTA) bound to a fiber with a glycerin binder.

A 321 gram amount of HBA pulp obtained from Weyerhaeuser Company (Tacoma, Wash.) was air-entrained in a blender-like mixing device and 50 grams of glycerin (supplied by Dow Chemicals of Midland, Mich.) were sprayed onto the fluff. Then 288 grams of disodium ethylenediamine tetraacetic acid (EDTA) (supplied by Mallinkrodt Chemical Works of St. Louis, Mo.) were added and mixed in the device. The blender was stopped, the product was vacuumed out, and spread out in a fume hood to dry overnight. The resulting product was examined by scanning electron microscope and revealed disodium EDTA particles attached to fibers as shown in FIG. 16.

EXAMPLE 9

A 321 gram amount of HBA pulp (a crosslinked high bulk fiber available from Weyerhaeuser Company, Tacoma Wash.) was air-entrained in a blender-like mixing device and 50 grams of glycerin (supplied by Dow Chemical of Midland, Mich.) were sprayed onto the fluff. Then 288 grams of sodium bicarbonate (supplied by J.T. Baker Chemical Co. of Phillipsburg, N.J.) were added and mixed in the device. The blender was stopped, the product was vacuumed out, and spread out in a fume hood to dry overnight. The resulting product was examined by scanning electron microscope and revealed fibers with attached sodium bicarbonate particles.

EXAMPLE 10

An NB 416 pulp sheet (southern bleached kraft available from Weyerhaeuser Company of Tacoma, Wash.) was treated with glycerin on a roll coater so that the product contained 10% glycerin by weight. That pulp sheet was fed into a hammermill and ground while simultaneously adding a polyacrylate hydrogel (IM 3900, supplied by Hoechst Celanese of Portsmouth, Va.) and ethylenediamine tetraacetic acid to the mill at rates such that the product contained 54% treated fiber, 42% IM 3900, and 4% EDTA. That mixture was shunted to an airlay device from M & J Machines (of Horsens, Denmark) and airlaid into a continuous web. The resulting product was examined by scanning electron microscope and revealed fibers with attached polyacrylate hydrogel and EDTA particles.

EXAMPLE 11

A procedure similar to the one described in Example 10 was performed using Kitty Hawk pulp (a thermobondable blend of southern bleached kraft and polyethylene fibers available from Weyerhaeuser Company of Tacoma, Wash.). The resulting product was thermobonded by passing the web through a through-air oven at 140° C. for 0.5 minutes. The resulting product was examined by scanning electron microscope, and revealed fibers with attached polyacrylate hydrogel and EDTA particles.

EXAMPLE 12

Figure 14:
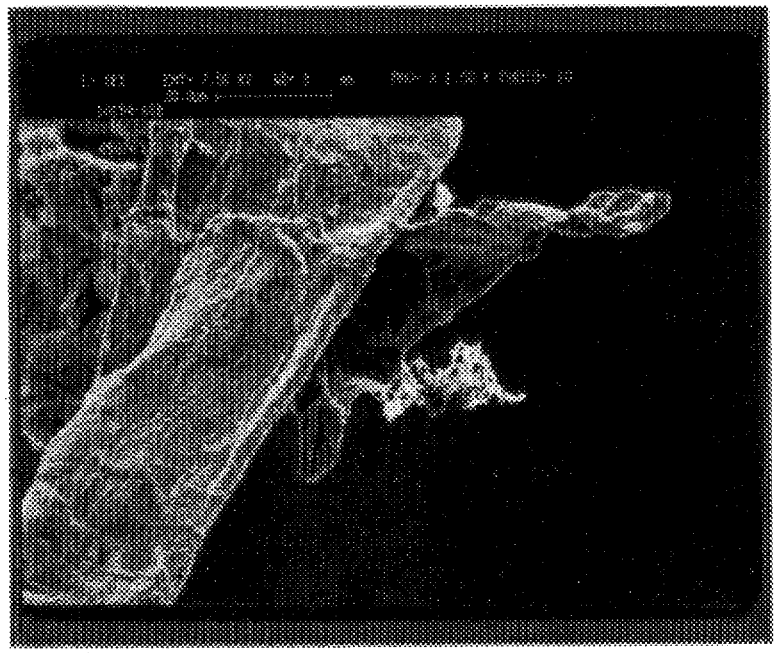
FIG. 14 is a photomicrograph of oxalic acid particles bound to a fiber with a glycerin binder.

In this example, oxalic acid is bound to the fibers by the binders of the present invention. A pulp sheet with 10% binder was prepared as in Example 10. The pulp sheet was conditioned at 90% relative humidity for 4 hours, then the sheet was fiberized in a Waring blender. Particles of oxalic acid were then added to the blender and blending continued. The product was dried and an SEM obtained, which is shown in FIG. 14. The feathery particle of oxalic acid is shown near the center of the photograph bound to the cellulose fiber by the glycerin.

EXAMPLE 13

Figure 15:
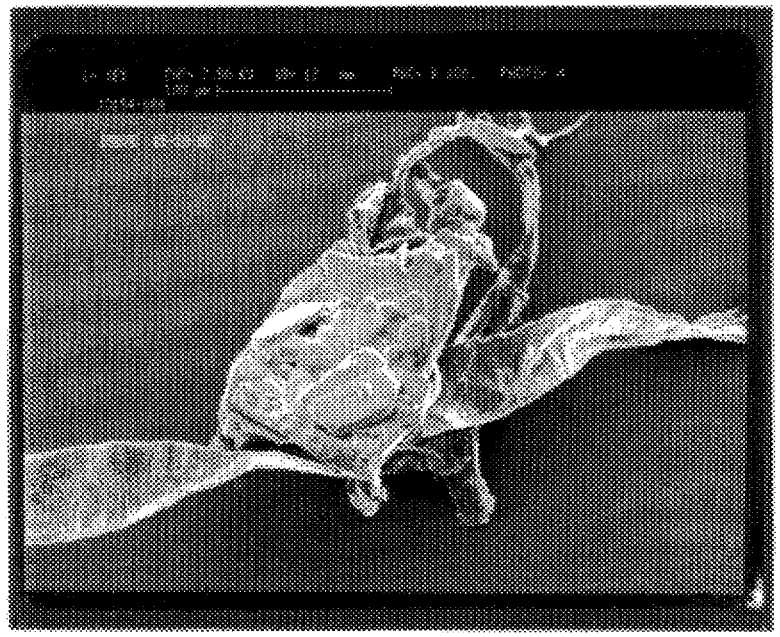
FIG. 15 is a photomicrograph of aluminum sulfate (alum) bound to a fiber with a glycerin binder.

Fibers were prepared as in Example 12, except aluminum sulfate (alum) was substituted for oxalic acid. The SEM of alum bound to the fibers is shown in FIG. 15.

X. Product Characteristics

The following examples illustrate how SAP retention, pad integrity, wettability, bulk and liquid retention are affected by the glycerin binder of the present invention.

EXAMPLE 14

Superabsorbent particles were bound to cellulose fibers with a glycerin binder, as described in Example 1 above. For purposes of comparison, superabsorbent particles were bound to a separate sample of cellulose fibers using a polyvinyl acetate (PVAc) binder that was about 3% carboxylated, that is only about 3% of the PVA monomers were carboxylated. Binding was performed as in Example 1, but PVAc was substituted for glycerin. A 100-gram sample of the glycerin and PVAc treated fluff with attached SAP was fed into a fan that was connected by a hose to a small cyclone mounted on top of a material containment box. This was done in an effort to simulate forces of mechanical agitation the fluff would encounter during the airlay process. After collection in the material containment device, fiber with attached SAP was removed and weighed. A five gram sample of the fiber with attached SAP was then placed in a column of sieves with decreasing mesh sizes and subjected to a shaking and thumping action for ten minutes in order to further dislodge any poorly attached SAP. Unattached or poorly attached SAP sifted through screens having a range of 5–60 mesh, while the fiber with well attached SAP remained on the 5 mesh screen.

A 2.00 gram sample of the fibers that remained near the top of the sieve column was then placed in a 75 ml sample of 0.9% saline for exactly one minute. After that minute, the liquid that was not absorbed was poured off into a separate, tared beaker and weighed. The relative amounts of liquid absorbed is indicative of the amounts of SAP bound to the fiber. Fiber retaining higher amounts of SAP tend to absorb more liquid and give a smaller amount of liquid not absorbed.

These results are shown in Table IV:

TABLE IV

Glycerin Binder
Comparing SAP Retention with Glycerin and PVAC Binders

| Binder | Beaker result |
| --- | --- |
| 40–504 (PVAc) | 22.8 g |
| 3666H (PVAc) | 22.0 g |
| Glycerin | 5.5 g |

Table IV illustrates that the glycerin binder provides a product that has an absorbency increase of 400% compared to the PVAc binder. A substantial portion of this improvement is believed to be due to better adhesion between the fibers and SAP, such that the particles are not dislodged from the fibers.

EXAMPLE 15

Pad integrity was compared in fibrous products that used no binder and a glycerin binder at 7% and 11% by weight. Each of these binders was used to bind SAP to fibers as in Example 6, and properties of the pad were measured and are shown in Table V:

TABLE V

Tensile Results

| Sample | Basis Weight | Density | Tensile Index |
|---|---|---|---|
| Pad integrity (low density): | | | |
| NB-416 (control) | 464 gsm | 0.12 g/cc | 0.257 Nm/g |
| NB-416/7% Glycerin | 437.6 gsm | 0.126 g/cc | 0.288 Nm/g |
| NB-416/11% Glycerin | 402.5 gsm | 0.135 g/cc | 0.538 Nm/g |
| Pad Integrity (high density): | | | |
| NB-416 (control) | 482.1 gsm | 0.218 g/cc | 0.475 Nm/g |
| NB-416/7% Glycerin | 460.7 gsm | 0.219 g/cc | 0.882 Nm/g |
| NB-416/11% Glycerin | 421.6 gsm | 0.248 g/cc | 1.536 Nm/g |

The glycerin binder in this example produced a product that had a higher tensile index than an untreated product. The increased tensile strength was especially enhanced in the densified (high density) product, and particularly when at least 11% of the binder was used.

EXAMPLE 16

The effect of binders on the wettability and bulk of fibers was tested using the following fibers: NB-316 (a standard southern bleached kraft pulp with no binder); GNB 25% is in this application is a designation for a standard southern bleached kraft pulp with 25% glycerin (entrained and sprayed); HBA pulp (a high bulk intra-fiber crosslinked fiber available from the Weyerhaeuser Company that contains intrafiber covalent crosslinks); and GHBA in this application is a designation for HBA fibers treated with a glycerin binder in amounts of 12.5% and 25% by weight. Results are given in Tables VI and VII.

FAQ time was determined by airlaying a specific quantity (4.00 grams) of the fluff to be tested into a clear plastic tube that was fitted with a screen at one end. The fluff and tube were then placed into a well in the test device and a metal plunger was lowered onto the fluff and the pad's bulk calculated. Water then flowed from underneath the pad, passed through the screen and wicked up through the pad. Absorbency time was measured from when the liquid makes contact with the bottom screen until the water completes an electrical circuit by contacting the foot of the plunger resting on top of the pad. Lower absorbency times indicate better absorbency. Since the absorption of the liquid by the pad was accompanied with some collapse of the pad's structure, the bulk of the wet pad was then recalculated. The amount of liquid absorbed was then measured and a gram-per-gram capacity for the material was calculated.

Table VI gives FAQ time as a measure of wettability. A lower FAQ time indicates a product that is more absorbent and wicks faster. Table VII gives wet bulk of fibers and the adjusted bulk of the fibers. The adjusted bulk is a calculated number obtained by dividing the bulk by the actual percent of pulp in the sample.

TABLE VI

Wettability

| Fiber | FAQ time |
|---|---|
| NB-316 | 3.0 sec |
| GNB 25% | 3.2 sec |
| HBA | 13.5 sec |
| GHBA 12.5% | 4.5 sec |
| GHBA 25% | 0.4 sec |

TABLE VII

Bulk

| Fiber | Wet Bulk | Adjusted Bulk |
|---|---|---|
| NB-316 | 12.7 cc/g | 12.7 cc/g |
| GNB 25% | 10.9 cc/g | 14.5 cc/g |
| HBA | 19.4 cc/g | 19.4 cc/g |
| GHBA 12.5% | 16.1 cc/g | 18.4 cc/g |
| GHBA 25% | 14.9 cc/g | 19.9 cc/g |

The low FAQ times (Table VI) in the glycerin-treated fibers (GNB, GHBA) show that wettability is as good as the untreated fiber (NB-316). The GHBA 25% had significantly better wettability than untreated HBA. Bulk of glycerin treated fibers (Table VII) was not significantly decreased or changed at all levels of glycerin binder on a fiber to fiber comparison basis.

EXAMPLE 17

Liquid retention of bound fibers was determined and compared to fibers in which no binder was added. NB-316 is a pulp sheet available from Weyerhaeuser Company in which no binder is used. HBA pulp is described in Example 20. HBA/Gly SAP was an HBA fiber that was bound with glycerin (12% binder, 48% fiber) and which contained 40% SAP particles. NB-316/Gly SAP is NB-316 fibers to which glycerin and SAP fibers were added.

The procedure for determining liquid retention was to weigh triplicate small portions (near 0.2 grams) of samples to the nearest 0.0001 gram and then heat-seal the small portions inside an envelope of a heat-sealable, nonwoven tea bag. The samples were then immersed in an excess of 0.9% saline for thirty minutes, then drained by suspending them from a clip for fifteen minutes. The samples were weighed to determine the amount of liquid absorbed. The grams of liquid absorbed per gram of sample were calculated and the samples were spun in a centrifuge for one minute. The samples were then reweighed and a percent-liquid-retention was calculated.

Results are shown in the following Table VIII:

TABLE VIII

Liquid Retention (after centrifuge)

| Fiber/Binder | % Retention |
|---|---|
| NB-316/none | less than 1% |
| HBA/none | less than 1% |
| HBA/Gly SAP | 23% |
| NB-316/Gly SAP | 31.5% |

The results in Table VIII illustrate that fibers that have SAP bound to them retain liquid well, while fibers without SAP retain liquid poorly. The glycerin binders provided excellent adherence of SAP to the fibers.

XI. Auxiliary Binder

As previously described, an auxiliary binder or additional binder or binders can be used in addition to the present binders or combinations thereof in accordance with the present invention. However, the additional binder(s) is selected to not react with the binder or binder combination of the present invention in a manner which prevents this latter binder from having the required functionality. Thus, the preferred auxiliary binders are non-reactive in this way. In addition, binders of the invention may be combined with one another and with other binders as long as they do not block the desired functionality.

EXAMPLE 18

A 321 gram amount of a southern bleached kraft fiber (NB-416, supplied by Weyerhaeuser) was air entrained in a blenderlike mixing device and sprayed with 212.8 grams of a polyvinylacetate latex (PN-3666H, supplied by H B Fuller of Minneapolis, Minn.). While still mixing, 438 grams of a water swellable polyacrylate hydrogel (Favorsab 800, supplied by Stockhausen of Greensboro, N.C.) was added and the resulting mixture was then sprayed with 100 grams of a 50% solution of glycerin (supplied by Dow of Midland, Mich.). The blender was then stopped and the mixture was vacuumed from the blender and placed in a fume hood to air dry overnight. The dried product was then airlaid into a 6" diameter pad in a laboratory padformer, pressed to a density of approximately 0.077 g/cc, and thermobonded at 140° C. for thirty seconds. The resulting pads had 40% bound SAP and improved tensile strength as compared to untreated fluff with SAP and as also compared to binder treated fluff with SAP without the auxiliary binder.

Tensile strength was highest with polyvinylacetate alone, followed by a combination of polyvinylacetate and glycerin, then glycerin alone. Lowest tensile strength was seen with no binder at all.

EXAMPLE 19

Binders of the present invention may be used to bind particles to pulp fibers that contain synthetic thermobonding fibers. In this example, Kitty Hawk pulp (available from Weyerhaeuser Company) is a mixture of NB316 southern bleached kraft and 22% polyethylene thermoplastic binder fibers. The Kitty Hawk pulp is used to produce a pulp web, with SAP bound to the fibers as described in Example 3. The web with adhered SAP is then passed through a thermobonder to soften the polyethylene fibers and fuse the fibers of the web to each other to increase web strength.

XII. Spectroscopic Evaluations

Spectroscopic measurements were made of the fiber products made according to the present invention. The results of the NMR studies are presented below.

A. NMR Analysis

EXAMPLE 20

The hydrogen nuclear relaxation time constants listed below were measured by nuclear magnetic resonance spectrometry (NMR), and reflect molecular motion at slow speeds (close to 45 kHz). Both glycerin hydrogen signals have significantly lower relaxation times in the ternary pulp/SAP/glycerin composite than in either of the binary composites. This indicates that molecular motions of glycerin in the ternary system are slower than in the two-component systems; that is, the combination of pulp and SAP bind glycerin more tightly than either pulp or SAP alone. Since neither covalent nor ionic bonding is operative in these composites, this increased binding would have to be the result of hydrogen bonding of glycerin by both pulp and SAP.

Hydrogen Nuclear Relaxation, $T_{1pH}$, at 45 kHz for Glycerin in Freshly-Prepared Samples.

| Sample | $T_{1pH}$, msec (std. devn.) | |
| --- | --- | --- |
| Components | —OH, $H_2O$ Peak | —$CH_2$—, —CH— Peak |
| SAP/Glycerin | 34 (11) | 30 (6) |
| Pulp/Glycerin | 5.8 (0.1) | 5.4 (0.2) |
| Pulp/SAP/Glycerin | 4.3 (0.3) | 4.3 (0.3) |

XIII. Activation

The binders of the present invention have the advantage of being activatable from an inactive state on the fibers by addition of liquid, heating, or by kinetic energy such as may be supplied by mechanical agitation or ultrasonics. Hence, a liquid binder can be applied to cellulose fibers, loose or in another form, such as a cellulose mat, in the absence of the particles to be bound. The binder is then dried or allowed to dry, for example until the binder and fiber reach an equilibrium moisture content with ambient air. Alternatively, the binder can be applied as a solid, for example, particles sprinkled onto a fiber mat. At a later stage of processing, a liquid such as water is added to the fibers resulting in an activation of the binder. The particulates may then be added, and the binder secures the particulates to the fibers. This subsequent processing of the fibers to attach the particles can occur, for example, at a separate location from the location where the binder was applied to the fibers. Therefore, manufacturers of products can add particulates of interest (e.g., superabsorbent particles or fibers; antimicrobial particles, etc.) at the place of manufacture of the end products that incorporate the treated fibers. Also, more than one type of particulate material (including water soluble and water insoluble particles) may be added, if desired. Particles without the required functionality would not be bound in the same manner.

It also has been found that some of the binders of the present invention can be activated by mechanical agitation (the application of kinetic energy). For example, glycerin binder may be applied to fibrous cellulose. The glycerin binder may be allowed to dry, and the fibers then mechanically agitated in the presence of superabsorbent particles and/or other particles to activate the glycerin binder and bind the particles to the fibers. Mechanical agitation may take place, for example, in a defiberizer where a sheet or mat of glycerin treated cellulose fibers are defiberized while being intimately mixed with SAP that is bound to the fibers by the mechanical agitation.

XIV. Binder Activation Examples

Binder activation in the present invention allows binder to be added to fibers either before or after particles are added to the fibers. The binder is subsequently activated by addition of liquid, heat, or by kinetic energy such as resulting from agitation, and particles are bound to the fibers. The particles may be added to the fibers either before binder activation, after binder activation, or simultaneous with activation. If SAP and/or other particles are to be added to cellulose fibers, for example, the binder may be applied to a pulp sheet which is subsequently fiberized. A liquid such as water may be added to the pulp before or after fiberization, and SAP may be added before or after water addition, or simultaneously with the water. If SAP is added after water addition, the SAP should be applied to the fibers prior to complete evaporation of the added water from the fibers. Water also can be added in other ways, such as by very humid air, a fog or mist, or as steam.

Activation can be of all the fibers, or only portions of the fibers, such as target zones or portions of the mat where particulate binding is desired. The particles may then be added to the mat and adhered to the target zones of the mat which have been activated. In some embodiments, the binder is applied as a solid and heated during a later processing stage to activate the binder by softening it such that it binds the particles to the fibers. The particles may be added in a pattern corresponding to a desired distribution (for example a non-homogeneous distribution) of particles in the fibrous material. Most commonly, however, activation is accomplished by using a binder solvent to moisten a targeted area of the product into which an inactive (dry or dried) binder has already been introduced.

In yet other embodiments, the binder is applied to the fibers and then activated by applying kinetic energy to the fibers. Neat dipropylene glycol binder, for example, may be sprayed on fibers and allowed to air dry. Desired particles are then added to the fibers as the fibers are mechanically agitated in a blender or defiberizer to kinetically activate the binder and bind the particles to the fibers. For kinetic activation, the binder may be added as a liquid or a solid to the fibers. In the case of liquid addition, the liquid is allowed to air dry, and then activated by mechanically agitating the fibers and binder. In the case of solid binder addition, the binder is applied as a solid, and then moistened (for example, to a total fiber moisture content of about 7%) and then mechanically agitated.

Activation of the binder may be performed prior to adding the particles, subsequent to adding the particles, or simultaneously with addition of the particles. Once the binder is activated, it adheres a substantial portion of the particles to the fibers, wherein "a substantial portion" refers to about half of the particles added, at least where the particles are not added in excess. Of the particles that are adhered, at least half of them (and more typically substantially all of them, e.g., over 80%) are adhered to the binder by non-covalent bonds, namely hydrogen bonds or coordinate covalent bonds, and the binder is in turn adhered to the fibers by hydrogen bonds.

In embodiments in which the binder is applied to the fibers as a solid, the activating step can comprise applying a liquid to the fibers after the binder has been applied to the fibers, shortly before the binder is applied to the fibers, or simultaneously with application of the binder to the fibers.

The activating step may be performed after the curing step is complete, if a curing step is to be performed.

The following example will illustrate several specific applications of the activation process, and are not intended to limit the invention to the disclosed methods.

EXAMPLE 21

The method of Example 1 above could be modified such that the SAP is not added until after the web is heated to 140° C. A solid urea binder could be substituted for the binder of Example 1, and it would melt well below 140° C., and in its liquid form bind the SAP to the fibers. The SAP could be applied randomly across the heated product, or applied specifically to a targeted zone of the product where enhanced absorbency is specifically desired.

EXAMPLE 22

A southern kraft pulp sheet was sprayed with a 75% solution of urea and allowed to air dry overnight. The sheet was then misted with water to raise its moisture content to 17–20% as it was fed into a Fitz hammermill filled with a three-eighths inch hole screen. Polyacrylate hydrogel particles of FAVOR 800 supplied by Stockhausen was simultaneously added to the mill by a screw feed device, mixed with the fluff, shunted to an M & J airlay forming machine and airlaid to form a web containing bound SAP throughout the web, i.e., without being confined to a surface of the web. Mixing SAP throughout the fluff helps produce a product in which SAP is homogeneously or randomly distributed, which diminishes problems of gel blocking.

EXAMPLE 23

A 900 gram amount of Kitty Hawk pulp sheet (from the Weyerhaeuser Co., containing 22% synthetic fibers) was immersed in a 10% by weight solution of urea (supplied by Aldrich of Milwaukee, Wis.) for thirty minutes. The 5-inch-wide sheet was then uncoiled on a lab bench to air dry overnight, heated in an oven at 80° C. for thirty minutes and conditioned in a 50% relative humidity chamber overnight. The sheet was then gravimetrically determined to be about 30% by weight urea. The sheet was fed into a Fitz hammermill fitted with a three-eighths-inch hole screen, defiberized, shunted to an M & J airlay line, and airlaid into a web. As the web emerged, the binder in the dried web was activated by misting target zones of the web with deionized water in a circular pattern from a spray bottle to raise the moisture content of the web or the target zones to 17–21%. Five gram aliquots of polyacrylate hydrogel (FAVOR 800 supplied by Stockhausen of Greensboro, N.C.) were subsequently sifted onto each activated target zone. The web that resulted contained target zones with 5 grams of SAP attached to the fibers in each target zone. Alternative spray patterns could be provided by selecting spray heads or different control devices that mist different patterns.

XV. Thermoplastic Binders

An auxiliary binder also may be used to help bind fibers to each other above the melting point of the auxiliary binder. The auxiliary binder may be a solid thermoplastic material that is applied to the fibers and softened by elevating the temperature during the binding step to above the softening temperature of the auxiliary binder. The auxiliary binder is thereby temporarily softened, rendered more fluid and subsequently resolidified as the temperature cools, which thermoplastically binds the fibers to each other, and the particles to the fibers. The auxiliary binder may also contain a hydrogen bonding functionality that hydrogen bonds the particles to the fiber. Examples of auxiliary binders that are thermoplastic and also contain hydrogen bonding groups include ethylene vinyl alcohol, polyvinyl acetate, acrylates, polycarbonates, polyesters and polyamides. Further information about the use of such auxiliary binders can be found in U.S. Pat. No. 5,057,166.

The auxiliary or second binder can be added to the fibers, either before or after a first binder, to help bind the fibers to each other and provide additional binding between the fibers and particles. A suitable second binder would be a thermoplastic or thermosetting binder. In the case of thermoplastic polymers, the polymers may be a material which remains permanently thermoplastic. Alternatively, such polymers may be a material which is partially or fully crosslinkable, with or without an external catalyst, into a thermosetting type polymer. As a few specific examples, suitable thermoplastic binders can be made of the following materials: ethylene vinyl alcohol, polyvinyl acetate, acrylic, polyvinyl acetate acrylate, acrylates, polyvinyl dichloride, ethylene vinyl acetate, ethylene vinyl chloride, polyvinyl chloride, stytens, styrene acrylate, styrene/butadiene, styrene/acrylonitrile, butadiene/acrylonitrile, acrylonitrile/butadiene/styrene, ethylene acrylic acid, polyethylene, urethanes, polycarbonate, oxide, polypropylene, polyesters, and polyimides.

In addition, a few specific examples of thermoset binders include those made of the following materials: epoxy, phenolic, bismaleimide, polyimide, melamine/formaldehyde, polyester, urethanes, urea, and urea/formaldehyde.

More than one of these materials may be used to treat the fibers. For example, a first coating or sheath of a thermoset material may be used followed by a second coating of a thermoplastic material. The superabsorbent particles or other particles are then typically adhered to the outer binder material. During subsequent use of the fibers to make products, the thermoplastic material may be heated to its softening or tack temperature without raising the thermoset material to its curing temperature. The remaining thermoset material permits subsequent heating of the fibers to cure the thermoset material during further processing. Alternatively, the thermoset material may be cured at the same time the thermoplastic material is heated by heating the fibers to the curing temperature of the thermoset with the thermoplastic material also being heated to its tack temperature.

Certain types of binders enhance the fire resistance of the treated fibers, and thereby products made from these fibers. For example, polyvinyl chloride, polyvinyl dichloride, ethylene vinyl chloride and phenolic are fire retardant.

Surfactants may also be included in the liquid binder as desired. Other materials may also be mixed with the liquid binder to impart desired characteristics to the treated fibers. For example, particulate material, such as pigments, may also be included in the binder for application to the fibers.

XVI. Application of Binder

The binders of the present invention can be added to the fibers in any convenient manner. One such procedure is to spray the binder or binders on a web of the fibers that is conveyed past a sprayer on a conveyor belt. Alternatively, loose fibers may be allowed to fall past a sprayer, or loose fibers may be moved on a conveyor belt past a sprayer. The loose fibers may also be slurried with or immersed in binder. It is also preferable to roll coat the binders on the web, particularly if the binder is viscous. For solid binders, blending of the fiber and binder may be accomplished or the binder may simply be sprinkled onto or otherwise comingled with the fibers, followed by a fixation step such as addition of heat or liquid. The fibers may also be sprayed or immersed in the binder, or binder particles may be applied thereto. These fibers can, while still wet in the case of a liquid binder or following activation of a liquid or solid, be combined with the particles.

The fibers also can be allowed to dry for later activation with an activation fluid, such as an activation liquid, and combined with the particles at that time. An example of when it may be desirable to apply the binder to the fiber and thereafter activate the binder in the presence of particles is when the particles are added at a remote site. For instance, the binder may be activated from an inactive state at a second location that is remote from a first location where the binder is applied to the fibers. The second location may be, for example, a location where a manufacturer combines fibers and particles into articles, such as absorbent articles. Particles may be added from conventional volumetric feeders in a hammermill or from injectors on a paper making line.

One method for uniformly coating the fibers with a binder and adding the particles is shown in U.S. Pat. No. 5,064,689. However, the invention is not limited to any specific mechanism for combining the fiber, binder and particles.

XVII. Production of High Bulk Fibers

Production of high bulk fibers with intrafiber crosslinks is known in the art. Processes for making such fibers are described in EP 440 472 A1; EP 427 317 A2; EP 427 316 A2; and EP 429 112 A2, as well as U.S. patent application Ser. No. 07/607,268 filed Oct. 31, 1990, and its published European counterpart. These high bulk fibers may be used in the present invention, with particles bound to them by the binders disclosed herein. Since methods of making high bulk fibers are known, only a brief description of one such process is given below.

A. Overall System

The apparatus 110 (FIG. 3) of the present invention comprises a conveying device 112 for transporting a mat 114 of cellulose fibers or other fibers through a fiber treatment zone 116; an applicator 118 for applying a treatment substance such as a crosslinking substance from a source 119 thereof to the mat 114 at the fiber treatment zone 116; a fiberizer 120 for completely separating the individual cellulose fibers comprising the mat 114 to form a fiber output comprised of substantially unbroken cellulose fibers substantially without nits or knots; and a dryer 122 coupled to the fiberizer for flashevaporating residual moisture from the fiber output and for curing the crosslinking substance, thereby forming dried and cured cellulose fibers.

The mat 114 of cellulose fibers is preferably in an extended sheet form stored in the form of a roll 124 until use. It is normally not necessary that the cellulose fibers comprising the mat 114 be completely dry. Since cellulose is a hydrophilic substance, molecules thereof will typically have a certain level of residual moisture, even after air drying. The level of residual moisture is generally 10% wt/wt or less, which is not detectable as "wetness." FIG. 3 also shows that more than one supply, such as multiple rolls 124, of the mat 114 of cellulosic fibers can be simultaneously processed using the present invention.

At the fiber treatment zone 116, sprayers or other applicators 118 apply chemicals such as crosslinking agents to the mat. Typically chemicals are applied uniformly to both sides of the mat. The wetted mat passes between a pair of rollers 128 which assist in distributing the chemicals uniformly through the mat. Other applicators may also, of course, be used.

The crosslinking substance is a liquid solution of any of a variety of crosslinking solutes known in the art. If required, the crosslinking substance can include a catalyst to accelerate the bonding reactions between molecules of the crosslinking substance and cellulose molecules. However, many if not most crosslinking substances do not require a catalyst.

Preferred types of crosslinking substances are selected from a group consisting of urea derivatives such as methylolated urea, methylolated cyclic ureas, methylolated lower alkyl substituted cyclic ureas, methylolated dihydroxy cyclic ureas, and mixtures thereof. A specifically preferred crosslinking substance would be dimethyloldihydroxyethylene urea (DMDHEU). In addition, crosslinking substances can be polycarboxylic acids, such as citric acid. Crosslinking materials are known in the art, such as described in the previously mentioned Chung patent, U.S. Pat. No. 4,935,022 to Lash, et al., U.S. Pat. No. 4,889,595 to Herron, et al., U.S. Pat. No. 3,819,470 to Shaw, et al., U.S. Pat. No. 3,658,613 to Steijer, al., U.S. Pat. No. 4,822,453 to Dean, et al., and U.S. Pat. No. 4,853,086 to Graef, et al.

Suitable catalysts include acidic salts which can be useful when urea-based crosslinking substances are used. Such salts include ammonium chloride, ammonium sulfate, aluminum chloride, magnesium chloride, or mixtures of these or other similar compounds. Alkali metal salts of phosphorus-containing acids may also be used.

Figure 3:
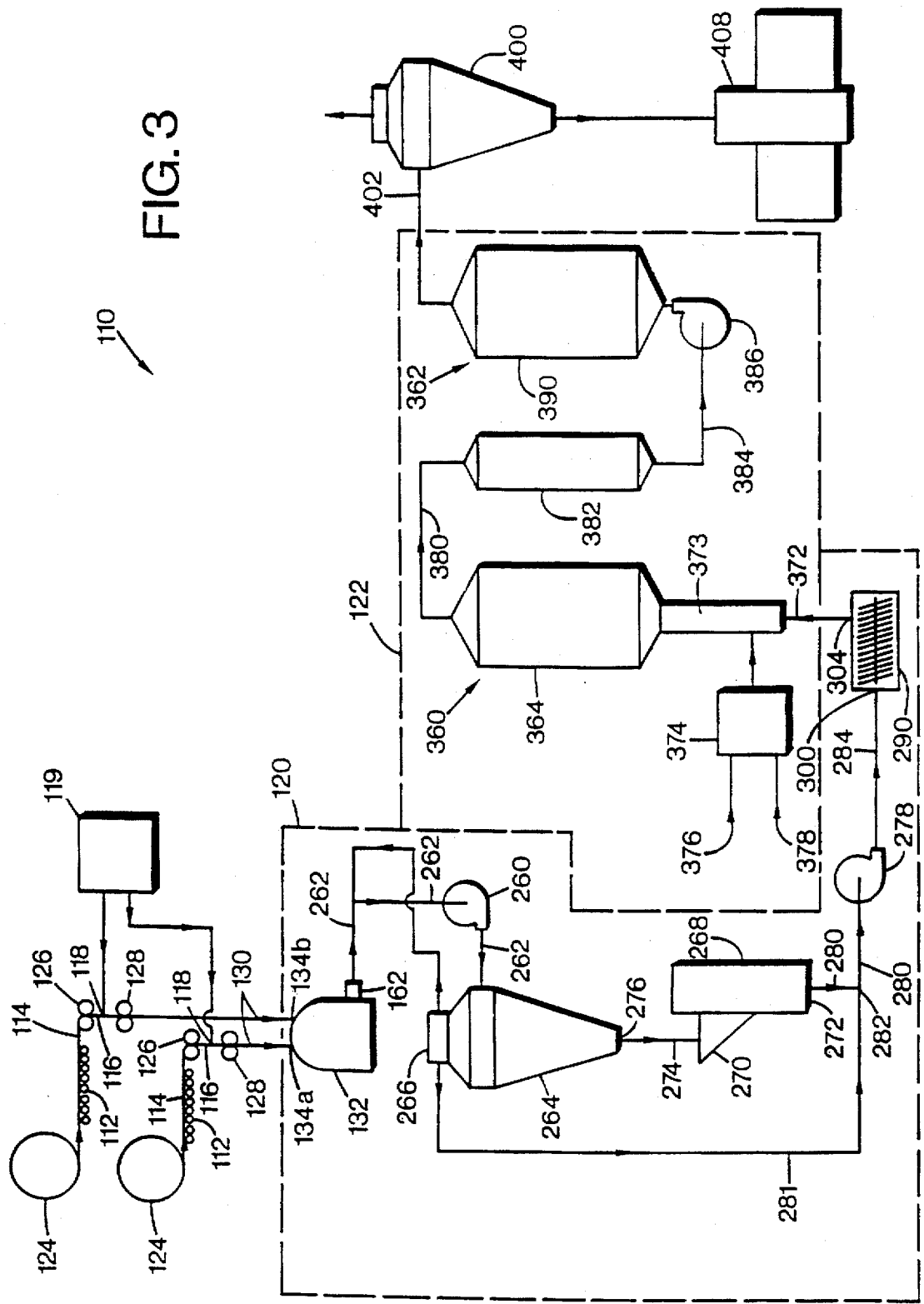
FIG. 3 is a schematic depiction of the components of an apparatus of the present invention that produce high bulk fibers.

In FIG. 3, the crosslinking substance applied to the mat 114 is obtained from a supply 119 thereof, such as a tank or analogous vessel.

Crosslinked cellulose fibers are individual fibers each comprised of multiple cellulose molecules where at least a portion of the hydroxyl groups on the cellulose molecules have been covalently bonded to hydroxyl groups on neighboring cellulose molecules in the same fiber via crosslinking reactions with extraneously added chemical reagents termed "crosslinking substances" or "crosslinking agents." Suitable crosslinking agents are generally of the bifunctional type which create covalently bonded "bridges" between said neighboring hydroxyl groups.

B. Conveying Device

Referring further to FIG. 3, each mat 114 of cellulosic fibers is conveyed by a conveying device 112, which carries the mats through the fiber treatment zone 116. FIG. 3 also shows a further portion of one type of conveying device comprised of a first pair of rollers 126 and a second pair of rollers 128 for each mat 114. The first and second pair of rollers 126, 128 are particularly effective for urging the corresponding mat at a substantially constant and controlled rate of speed.

C. Fiber Treatment Zone

Each mat 114 is urged by the first and second pair of rollers 126, 128 through the fiber treatment zone 116 where the mat 114 is impregnated with a liquid crosslinking substance. The crosslinking substance is preferably applied to one or both surfaces of the mat using any of a variety of methods known in the art useful for such a purpose, such as spraying, rolling, dipping, or analogous method. Combinations of spray and roller applicators can also be employed.

The crosslinking substance is typically applied in an amount ranging from about 2 kg to about 200 kg chemical per ton of cellulose fiber and preferably about 20 kg to about 100 kg chemical per ton of cellulose fiber.

D. Fiberizer

The next subsystem following the fiber treatment zone is a fiberizer 120 which serves to comminute one or more mats 130 impregnated with the crosslinking substance into individual substantially unbroken cellulose fibers comprising a fiber output.

Referring further to FIG. 3, a first conveyer fan 260 of conventional design can be utilized for propelling the fibers from the outlet 162 of the attrition device 132 through a conduit 262.

An optional component of the fiberizer 120 is a first cyclone 264 or similar apparatus known in the art, utilized in a conventional manner to concentrate the fibers passing out of the outlet 162 of the attrition device 132. The first cyclone 264 receives the fibers through the conduit 262 coupled thereto.

Excess air can be recovered at the top 266 of the first cyclone 264 and recycled as required through a conduit 268 to a location upstream of the first conveyer fan 260 (if used). Such additional air can be beneficial for easing the transfer of the fibers through the first conveyor fan 260.

A disk refiner 268 is another optional component of the fiberizer 120 which can be employed to effect additional separation of fibers (removal of knots) if required. The disk refiner 268 is of a type known in the art and comprises a disk refiner inlet 270 and a disk refiner outlet 272. A representative disk refiner 268 is type DM36 manufactured by Sprout-Bauer, Incorporated of Muncie, Pa. If the disk refiner 268 is used, the inlet 270 thereof is coupled via a conduit 274 to an outlet 276 of the first cyclone 264.

A second conveyor fan 278 may optionally be utilized to urge propagation of the fibers through a conduit 180 downstream of the disk refiner 268. Excess air can be recovered from the top 266 of the first cyclone 264 and routed via a conduit 281 to a tee 282 just upstream of the second conveyor fan 278.

Another optional component of the fiberizer 120 is a fluff generator 290 which receives the fibers from the optional second conveyor fan 278 through a conduit 284. The fluff generator is described in detail below and in copending U.S. patent application Ser. No. 07/607,157.

E. Dryer

Referring further to FIG. 3, a preferred embodiment of the present apparatus 110 includes a dryer 122 which is utilized to perform two sequential functions: remove residual moisture from the fibers and cure the crosslinking agent. Preferably, the dryer 122 comprises a drying zone 373 for receiving fibers, e.g. from fluff generator outlet 304 and for removing residual moisture from the fibers via a "flash drying" method and a second drying zone 360, 362 for curing the crosslinking agent. In FIG. 3, the curing starts in zone 360 and continues through zone 362.

The FIG. 1 embodiment shows that zone 373 is coupled to the fluff generator outlet by a conduit 372 and to a source 374 of heated air, typically produced by combustion of a supply of natural gas 376 and fresh air 378. The temperature of heated air is regulated to maintain the temperature of the drying zone 373 within a range of about 200° C. to about 315° C. As the fiber output passes into the drying zone 373, the wet fibers comprising the fiber output are substantially instantaneously exposed to the high temperature in this zone. Such rapid exposure to high temperature imparts a "flash drying" effect to the fibers, thereby causing rapid and thorough drying and separation of the fibers. The passage time through the drying zone 373 is preferably less than one second.

The FIG. 3 embodiment shows that the first zone 360 is comprised of a first tower 364 comprised of a body portion 366, an inlet 368, and a first tower outlet 370. The dryer zone 373 is coupled via a conduit 372 to the outlet of the fluff generator 290.

In FIG. 3, the first tower 364 is shown preferably coupled via a conduit 380 to a down tube 382, which is coupled via a conduit 384 to a third conveyor fan 386 located at an inlet 388 of a second tower 390. The third conveyor fan 386 transports the fibers through the dryer which thereby pass into the second tower 390. As the fibers are lofted through the second tower 390, they are still exposed to a curing temperature within a range of about 140° C. to about 180° C., which is sufficient to effect curing of the crosslinking agent without scorching the dry fibers. The lofting keeps the fibers separated until the crosslinking reaction is complete. The curing temperature depends upon the type of crosslinking material used to treat the fibers and also is set at a level so as to not scorch the fibers during curing. It should be noted that single stage dryers may also be used.

The dried and cured fibers exiting the dryer outlet of tower 390 have an extremely low level of nits and virtually no knots. Further, they are not discolored from scorching and the like, and have a median fiber length substantially unchanged from the median length of the fibers comprising the mat 14.

FIG. 3 also shows a second cyclone 400 of conventional design coupled via a conduit 402 to the outlet of tower 390, serving to concentrate the fibers passing therethrough in preparation for collection. The resulting concentrated fibers can be collected using any of a number of collection devices 408 known in the art, such as fiber bagging devices.

EXAMPLE 24

In this example, non-woven fibrous mats were impregnated with a crosslinking agent, fiberized, dried, and cured using the apparatus as diagrammed schematically in FIG. 3.

Two 52-inch-wide mats of southern pine kraft wood pulp fibers (type NB 316 from Weyerhaeuser Company) and having a basis weight of 680 g/m$^2$ were fed to the apparatus. The mats were impregnated using dimethyloldihydroxyethylene urea at a concentration of about 5%, applied over both sides of each mat using a combination of spray nozzles and impregnation rollers. The loading level of crosslinking agent was about 4.5% w/w (weight of binder relative to the weight of the fibers).

The treated fiber mats were fed at the rate of 8 meters/min to the attrition device 32. The specific attrition device used in this example was equipped with six mat inlets and a rotor having 16 rows of hammers as described above around the circumference of the rotor. The rotor had a diameter of 30 inches and was rotated at an angular velocity of 1200 rpm by an electric motor. Other rpm rates have also been tested and have proven satisfactory, including extremely high rpm rates.

Random samples of fibers were obtained from the output attrition device and observed for nits. These samples were 2.6 grams and were consistently observed to have fewer than three nits on the average with most samples having no nits. The attrition device was flushed with water once every sixteen hours for cleaning purposes.

A disk refiner was employed downstream of the attrition device. This specific disk refiner was a DM36 refiner as previously mentioned. A fluff generator as described in FIGS. 7–9 was also employed in this downstream of the disk refiner. The temperature at the dryer input in this example was within the range of 200° C. to 315° C. The temperature at the second tower outlet was within the range of 140° C. to 180° C. Crosslinked fiber at the output of the dryer was produced at a rate of about 5000 pounds per hour. The particle binders and particles of the present invention can be added before, after, or simultaneously with curing. The term "curing in the presence of the binder" means that the binder is added before or simultaneously with curing. Curing in the presence of the binder is not usually a problem because the binder cannot always participate in the intrafiber crosslinking reaction, and the binder is not affected by the curing step. In certain situations, however, the binder can also form covalent intrafiber crosslinks. Polycarboxylic acids (such as citric acid), polyols (such as dipropylene glycol) and polyamines (such as ethylene diamine) can function as crosslinking agents, and are consumed during the curing step in the formation of covalent crosslinks. Hence in the limited case in which the crosslinking agent is also a binder material, steps should be taken to prevent the binder from being consumed as a crosslinker in the curing step.

Formation of the intrafiber covalent ester bond requires an anhydride intermediate. Formation of the anhydride intermediate can be retarded by the presence of water. The present inventors have found that about 20% water (more preferably at least 30% water) by weight in the fibers will sufficiently retard curing so that adequate binder functional groups will remain available in the fibers to bind the particles to the fibers. Hence when curing the crosslinking material in the presence of a binder that is also a crosslinking material, the fibers should contain at least about 20% water by weight of the fibers when curing begins. When curing the crosslinking material in the presence of a binder that is not also a crosslinking material, steps to prevent covalent bond formation are not usually necessary. When the crosslinking material is not cured in the presence of the binder, that is when the binder is applied after curing, no steps need be taken to inhibit covalent bond formation.

XVIII. Composite Absorbent Product

In accordance with the present invention, absorbent structures or articles may be made from the fibers, with binder and adhered particulates. These articles may be composite structures (e.g., made of plural materials). For example, the articles may have a core of plural types of fibers, or fiber layers, with or without covering materials. These products are capable of absorbing significant quantities of water and other fluids, such as urine and other body fluids. Such products include, but are not limited to, disposable diapers, sanitary napkins, incontinent pads, towels and the like.

Figure 4:
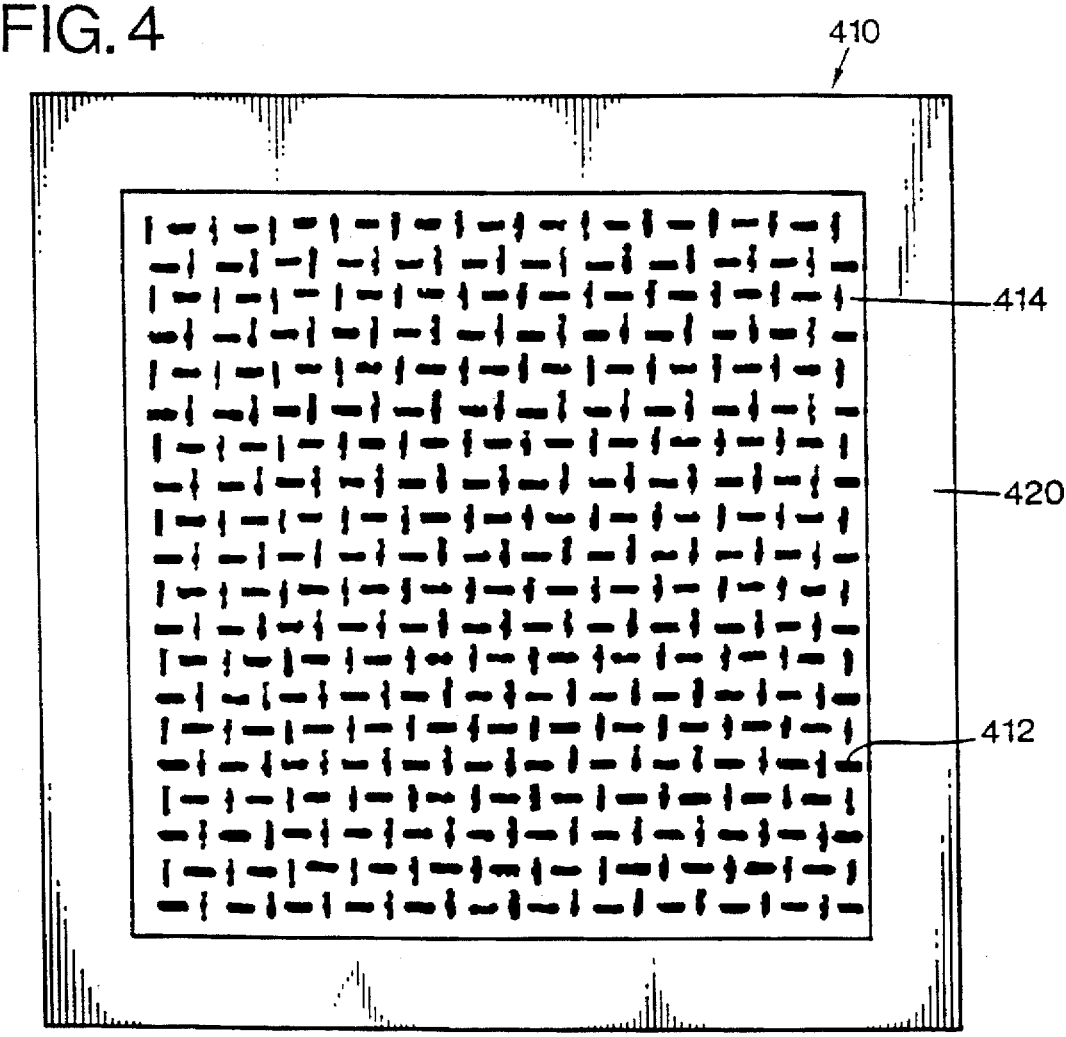
FIG. 4 is a top plan view of a structure into which fibers of the present invention are incorporated with attached particles, the fibers being in the form of an illustrated absorbent pad.
Figure 5:
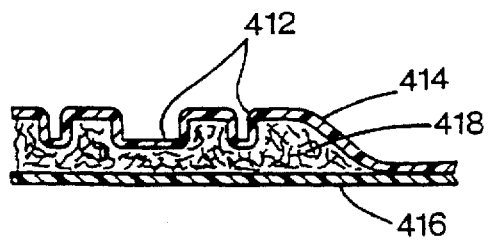
FIG. 5 represents a partial sectional view of the pad of FIG. 4.

FIGS. 4–5 illustrate an absorbent pad structure which may be formed from fibers of the present invention, whether or not they are blended with other fibers. FIGS. 4 and 5 represent an absorbent pad 410 having a heat embossed screen pattern 412. Pads having no pattern may also be used. A pad having a cover sheet 414 and a backing sheet 416 may be formed, for example, by placing a square fiber piece cut from the sheet onto a corresponding precut backing sheet. A corresponding precut cover sheet is placed over the top of the fiber 418 on the backing sheet. This assembly may then be adhesively bonded around a continuous margin 420.

With reference to FIGS. 6–7, an absorbent structure in the form of a bandage is shown. A bandage 430 for application to a wound to absorb blood and other bodily fluids is shown. An absorbent pad 440 is securely mounted to an exterior or pad mounting surface 434 of a backing strip 436. Fibers 441 are contained in pad 440, and particles are attached to the fibers 441 in accordance with the present invention. Any suitable mounting or securing means may be used to affix pad 440 to the surface 434 of the strip 436. However, it is preferable for surface 434 to be coated with an adhesive so that the pad 440 may be adhesively mounted in place. An exemplary adhesive is ethylene vinyl acetate adhesive. It is also desirable for the overall surface 438 of backing strip 436 to be coated with a conventional adhesive. Surface 438 is the surface which is affixed to the area of the skin surrounding the wound. Conventional "peel-back" tabs may be used to protect the adhesive coating and pad 440 until the bandage is to be applied. This type of backing strip is well known in the art.

The backing strip 436 may be of any known flexible material suitable for application to the skin. It is preferable for the strip 416 to be of a material which is impermeable to the passage of liquid so that fluid from a wound is contained by the bandage. However, the strip 436 may be apertured or otherwise breathable to permit air to reach the wound to promote the healing process. A specific example of a suitable backing strip 436 is a polyethylene film.

As in the other structures described, a variety of combinations of antimicrobials and other particles may be used in the fibers 441 of such a bandage. Again, however, the particles are adhered securely in place when the particles have a hydrogen bonding or a coordinate covalent bonding functionality, the fibers to which these particles are bound have a hydrogen bonding functionality and the binder has at least one functionality and one hydrogen or one coordinate covalent bonding functionality. Binders would include organic binders such as glycerin, a glycerin monoester, a glycerin diester, a polyglycerin oligomer, urea, propylene glycol, polypropylene glycol oligomer, and urea derivatives such as DMDHEU. Two different particles, such as antimicrobials in particulate form, may be adhered to the same fiber. In the alternative, each different type of antimicrobial particle or other particle may be adhered separately to different fibers. Also, blends of fibers may be included in absorbent structures such as pad 366. For example, these blends may include fibers with adhered antimicrobial (one or more antimicrobials) particles and adhered superabsorbent particles; fibers with one or more antimicrobial particles without superabsorbent particles blended with fibers having adhered superabsorbent particles with or without antimicrobial particles; and combinations of such fibers with untreated fibers and/or binder coated fibers without superabsorbent particles or antimicrobial particles. In addition, other particles, such as anticoagulants or hemostatics may be attached to the fibers.

The absorbent pad of bandage 430 may also include a cover sheet that is typically made of any suitable material which will readily permit the passage of liquid through the cover sheet to the fibers 441, such as nonwoven fiber webs of fibers such as, for example, rayon, nylon, polyester, propylene and blends thereof. One specifically preferred cover sheet material is a 70 percent rayon/30 percent polyester blend having a basis weight of 18 g/m² from Scott Paper Company.

Figure 8:
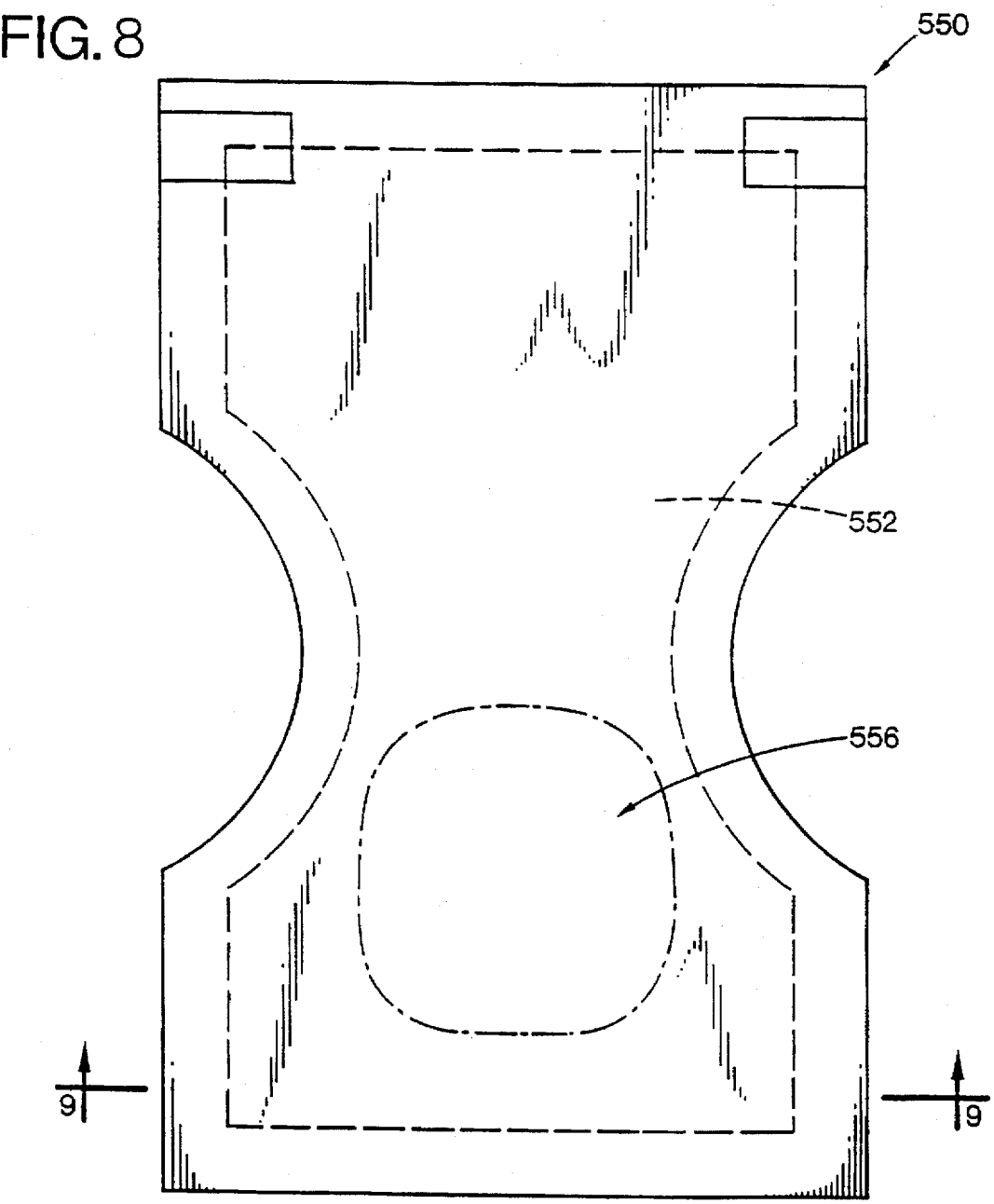
FIG. 8 is a plan view of a disposable diaper including a core of fibers of the present invention.
Figure 9:
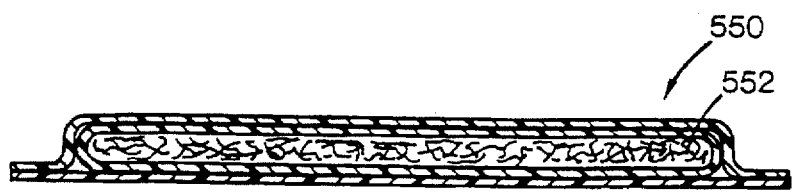
FIG. 9 is a vertical sectional view along line 11—11 of the diaper of FIG. 8.

FIGS. 8 and 9 illustrate a conventional disposable diaper 550 with a core 552 which is comprised of fibers of the present invention with adhered superabsorbent particulate materials. These particulate materials may be confined to a target zone (for example, the front or crotch portion of a diaper indicated at 556) or of a heavier concentration in the target zone. This can be accomplished by airlaying fibers of the present invention in such a zone. Also, the core may be activated by melting the binder or moistening the target zone with water. The superabsorbent particles may be sprinkled on or otherwise applied to this wetted zone. As the zone dries, the particles are adhered in place.

XIX. Densification

The products such as described above, as well as webs of the fibers of the present invention, can also be densified by external application of pressure to the web. The web could be densified by passing it through a set of calendar rolls set at 60 and 90 pli (pounds per linear inch, as in a calendar press) respectively to yield sheets with increased densities. Densification may alternatively be provided by compaction rolls or presses. The inventors have found that densification is facilitated in SAP-containing products treated with binders of the present invention, when the densification occurs with the binder in an active state. Products that are treated with these binders require less heat and pressure than untreated fibers to densify to a given density. Densification is preferably performed to produce a product that has a density of about 0.06 to 0.7 g/cc, more preferably 0.1 to 0.3 g/cc.

An example of densification using some of the binders of the present invention is given below:

EXAMPLE 25

The products of the present invention can be formed into 550 gram/square meter sheets, six inches in diameter, in a laboratory padformer. Those pads may be passed through a set of calendar rolls set at 60 and 90 pli, respectively to yield sheets with densities of 0.3 and 0.5 g/cc.

EXAMPLE 26

HBA with 40% IM 1000 F and HBA pulp with 12% glycerin and 40% IM 1000 F were formed into six-inch pads in the padformer then pressed at about 6500 psi for 15 seconds. HBA pulp without glycerin binder reached a density of 0.4 g/cc and HBA pulp with glycerin bound particles reached a density of 0.57 g/cc. This example illustrates that fibers treated with the method of the present invention achieve a greater density than untreated fibers at the same compression pressure.

XX. Water Addition

In some embodiments of the invention, a crosslinking material is added to the fibers and cured to form intrafiber covalent bonds that produce high bulk fibers. If the crosslinking material and binder are the same (for example, dipropylene glycol) are both different but capable of intrafiber crosslinking, and the binder is added before curing occurs, substantially all of the crosslinking material/binder will be used in the covalent crosslinking reaction, such that none will be available for subsequent binding of the particles to the fibers with hydrogen bonds or coordinate covalent bonds. In this particular instance (where the crosslinking material and binder are both capable of crosslinking, and are added before curing) water may be added to the fibers before curing to retard initiation of the curing step and ensure that a portion of the binder's functionality is not consumed in the crosslinking reaction. At least 20% water by weight in the fibers sufficiently retards intrafiber covalent bond formation to allow residual dipropylene glycol on the fibers to bind the particles to the fibers. The following example illustrates this process.

EXAMPLE 27

A 100 gram pulp sheet was sprayed with 44.5% intrafiber crosslinking material, and the pulp sheet was then delaminated and fed in small bits into a padformer while adding superabsorbent particles to delaminated pulp sheet at the same time. The material was run a second time through the padformer to fluff it up, and the material was then subsequently cured for 20 minutes in an oven at 150° C.

In a first run, the crosslinking material was a modified ethylene urea and citric acid, while the particulate material was IM 1000 F. To the 100 g pulp sheet was added 63.4 grams of the ethylene urea, 16.76 grams citric acid, and 70 grams of IM 1000 F, for a final crosslinker content of 35.2% ethylene urea and 9.3% citric acid, by weight. No water was added in this run.

In a second run, the 100 gram pulp sheet was crosslinked with 30.83 grams of a polyaldehyde (glyoxal), 5.03 grams of a glycol, 0.2 grams alum, 0.2 grams citric acid, and 15 grams distilled water. Curing was performed after 70 grams of IM 1000 F SAP was added to the pad.

Attachment of the particles to the pad was poor in both of these runs.

Each of these runs was then repeated, except 50 grams of distilled water was added before curing. Hence there was 15 g of water in the first run and 65 g of water in the second run. Particle attachment to the fibers was greatly improved.

Electron microscopic examination of the fibers from these runs showed that particle bonding did not occur in the absence of the 50 additional grams of water. In the presence of additional 50 grams of distilled water, however, electromicroscopic data showed actual bonding of the particles to the fibers.

XXI. Particulate Binding

Figure 10:
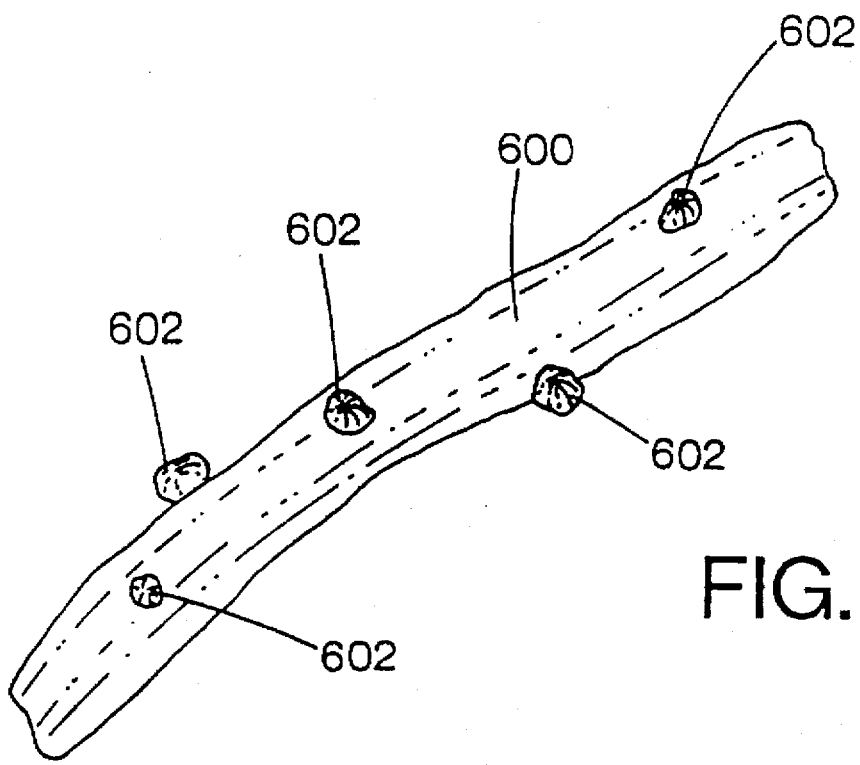
FIG. 10 is a view of an enlarged fiber with particles bonded to the fiber with the binders of the present invention.

FIG. 10 shows an isolated, enlarged cellulose fiber 600 with SAP particles 602 bound to it by a binder of the present invention. This drawing illustrates an example of the SAP retaining its discrete particulate form following binding to the fibers. Some particle to particle fusion may occur in accordance with this invention, but maintenance of a discrete particulate form excludes formation of a completely confluent film in which the particles lose their particulate identity. Such a confluent film produces gel blocking that interferes with efficient liquid absorption into the fibers.

The shown fiber 600 is elongated, and has an aspect ratio (ratio of length to width) of about 1000:1 to 5:1, preferably about 1000:1.

Figure 11:
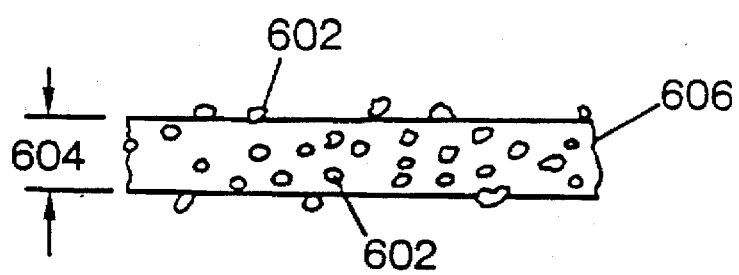
FIG. 11 is a schematic view of a cellulose mat with particles bound to all its surfaces and throughout its depth.

FIG. 11 shows the particles 602 distributed substantially uniformly throughout the depth 604 of a pad 606. The particles are also shown adhering to all the surfaces of the pad. Particles may be distributed in any desired pattern throughout the pad in accordance with this invention, and need not necessarily adhere to all surfaces or be distributed throughout the volume of the mat, or distributed uniformly.

As can be seen from FIGS. 10–11 (and FIGS. 12–15 discussed below), the particles are not encapsulated by the binders, but are instead chemically bound to the fiber at the interface between the particle and fiber. The particles and fibers of the present invention are not encapsulated with the binder. Moreover, the binder does not agglomerate the fibers together, and in many embodiments does not bind fibers to each other. Discrete individual particles retain their identity on the surface of the fibers, instead of being subsumed in a thermoplastic encasement around the fiber and particle.

XXII. Electron Photomicrographs

An electron photomicrograph of superabsorbent particles (SAP) bound to cellulose fibers with an urea binder is shown in FIG. 12.

The SAP is at the left margin of the photograph, and is fused to the fiber which occupies the central portion of the photomicrograph. The particle is seen to be fused to the fiber, and the fiber has undergone some shear damage that resulted in a fracture of the fiber. It is significant that the fiber has experienced shear damage while the particle has remained fused to the fiber, because this indicates that the particle-fiber bond formed by the ascorbic acid is very strong and resilient, resisting mechanical disruption.

Figure 13:
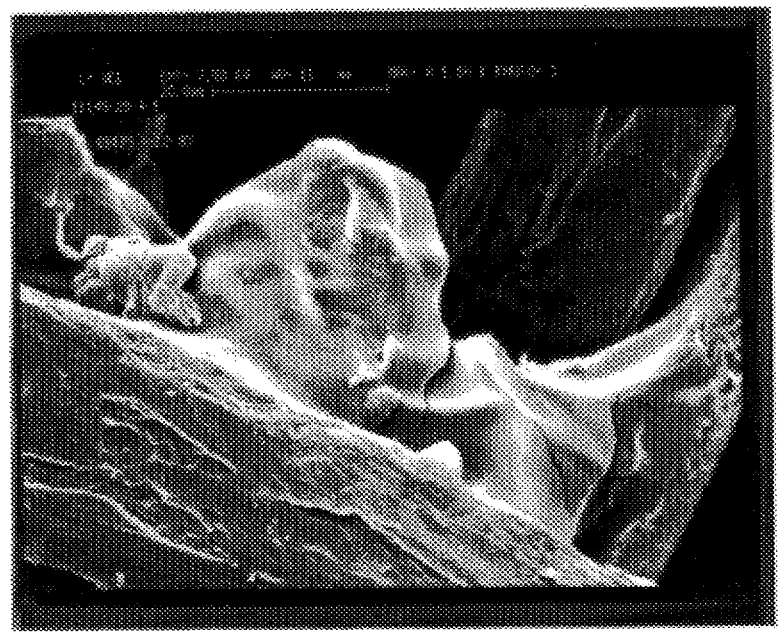
FIGS. 13 is a photomicrograph of a particle bound to fibers with glycerin and urea.

FIGS. 13 shows an electron photomicrographs that illustrates individual particles bound to fibers with a urea and glycerin binder. FIG. 13 shows that SAP retains its individual particulate form when adhered to the fiber with a lactose binder. The particles do not form a fused confluent mass without particulate identity.

EXAMPLE 28

An electron photomicrograph of oxalic acid particles bound to cellulose fibers with a glycerin binder is shown in FIG. 14. The bound oxalic acid is near the center of the photograph, and is seen fused to the fiber without mechanical encapsulation of the fiber and particle by an encapsulating binder.

FIG. 15 is an SEM illustrating a particle of aluminum sulfate (alum) bound to a cellulose fiber with a glycerin binder. The alum particle is seen at the center of the photograph, and the particle retains its individual particulate form when adhered to the fiber. The particles do not form a confluent mass lacking particulate identity. Moreover, the particles are not encapsulated by a material that mechanically holds the particle in contact with the fiber.

XXIII. Fiber Mixtures

The fibers of the present invention, such as fiber 600, can be mixed with other types of fibers, such as that disclosed in U.S. Pat. No. 5,057,166. The latex coated fibers of that patent can be mixed with the fibers of the present invention to produce an absorbent product that has characteristics of both types of fibers.

XXIV. Additional Binder Characteristics

U.S. Pat. No. 3,903,889 discloses a process for adhering absorbent particles to pulp fibers using syrup, honey, and other polysaccharides such as dextrins. An essential requirement of these adhesive agents is that they must possess the property of being permanently pliable, and not rigidifying into a brittle film. The binders of the present invention, in contrast, are capable of functioning as a binder after solidifying into a rigid crystalline material. Even the binders of the present invention that do not rigidify into a solid (such as glycerin and propylene glycol) are very hygroscopic, and can be present on fibers having a total water content of no more than 15%, or even 12%. This is in contrast to the adhesives such as honey and corn syrup disclosed in U.S. Pat. No. 3,903,889 that are not hygroscopic. Polysaccharides (such as corn syrup, honey and dextrins) are excluded as binders from some embodiments of the invention because they remain tacky upon drying. Tacky binders make processing the binder-coated fibers difficult. The polysaccharide polymers are also excluded from nonpolymeric embodiments of the binder of the present invention. Moreover, the nonpolymeric saccharides such as monosaccharides and disaccharides, lack the high viscosity and tacky-adhesive physical properties of polysaccharides such as corn syrup and honey. The nonpolymeric saccharides of the present invention may be solids, which avoid the viscosity and handling problems associated with polymers.

As used in this application, a particle that is soluble in water will completely dissolve at least 10 g of the particle in 300 ml water at 25° C. A particle that is sparingly soluble in the binder will completely dissolve no more than about 5 g of the particle in 300 ml of the binder at 25° C.

Some of the binders of the present invention are also water soluble. Some of the particles are soluble in the binder. However, such particles will suffice for the present invention if the amount of particle added is in excess of the saturation level of the particles in the binder. A binder that is soluble in water will completely dissolve at least 10 g of the binder in 300 ml water at 25° C.

Having illustrated and described the principles of the invention in many preferred embodiments, it should be apparent to those skilled in the art that the invention can be modified in arrangement and detail without departing from such principles. We claim all modifications coming within the spirit and scope of the following claims.

We claim:

1. A fibrous product made by the method comprising the steps:

providing fibrous material comprising individualized fibers having a hydrogen bonding functionality;

providing particles having a hydrogen bonding functionality or a coordinate covalent bond forming functionality;

selecting a binder from the group consisting of glycerin, a glycerin monoester, a glycerin diester, a propylene glycol, urea, and combinations thereof, the binder comprising binder molecules, the binder molecules having at least one functional group capable of forming a hydrogen bond or a coordinate covalent bond with the particles, and at least one functional group capable of forming a hydrogen bond with the fibrous materials; and exposing at least a portion of the particles to sufficient amounts of the binder in the presence of the fibrous material to bind at least a portion of the particles to the fibrous material.

2. The fibrous product of claim 1 wherein the binder is glycerin.

3. The fibrous product of claim 1 wherein the binder is urea.

4. The fibrous product of claim 1 wherein the binder comprises a mixture of glycerin and urea.

5. The fibrous product of claim 1 wherein the step of exposing at least a portion of the particles to the binder in the presence of the fibrous material comprises providing the binder on the fibrous material in the absence of the particles, allowing the binder to assume an inactive state, then later activating the binder from an inactive state in the presence of the particles and fibrous material by providing heat, an activating fluid, or by applying kinetic energy to the fibrous material and inactive binder.

6. The fibrous product of claim 1 wherein the fibers are wet pulp fibers in a wet-laid fiber sheet or web manufacturing line, and the binder is applied to the fibers while the fibers are on the wet-laid sheet or web manufacturing line.

7. The fibrous product of claim 1 wherein the step of exposing at least a portion of the particles to the binder in the presence of the fibrous material comprises providing the binder on the fibrous material in the absence of the particles, allowing the binder to assume an inactive state, then later activating the binder from an inactive state by adding water in the form of a liquid, steam or humid gas before, simultaneously with, or after exposing the particles to the binder in the presence of the fibrous material.

8. The fibrous product of claim 1 wherein the step of providing fibrous material further comprises providing individualized cellulose fibers that have hydrogen bonding functional sites, wherein the individualized fibers are cured in the presence of a crosslinking material to produce high-bulk fibers with intrafiber covalent crosslinks, and the fibers are fiberized to reduce interfiber bonding between the cured fibers.

9. The fibrous product of claim 8, wherein the particles comprise superabsorbent particles.

10. The fibrous product of claim 1, wherein the particles comprise superabsorbent particles.

11. The fibrous product of claim 1, further comprising the step of densifying the fibers and the bound particles by applying external pressure to the fibers.

12. The fibrous product of claim 11, further comprising the step of forming the fibers into a web or sheet before the densifying step such that the web or sheet is densified by applying external pressure to the web or sheet.

13. The fibrous product of claim 1, wherein the particles are soluble in water and are sparingly soluble in the binder.

14. The fibrous product of claim 13, wherein the method further comprises the step of activating the binder on the fibers from an inactive state by providing heat, an activating fluid, or by applying kinetic energy to the fibers and binder.

15. A fibrous product comprising:

individualized fibers having hydrogen bonding functionalities; and a binder selected from the group consisting of glycerin, a glycerin monoester, a glycerin diester, a propylene glycol, urea and combinations thereof, the binder comprising binder molecules, the binder molecules having at least one functional group capable of forming a hydrogen bond or a coordinate covalent bond with particles having a hydrogen bonding or a coordinate covalent bond forming functionality, and at least one functional group capable of forming a hydrogen bond with the fibrous material, wherein at least a portion of the particles can be bound to the fibrous material.

16. The product according to claim 15 wherein the binder is glycerin or urea.

17. The product according to claim 16 wherein the binder is present in an amount of from about 1 to about 40 percent based on the weight of the product.

18. The product according to claim 15 wherein the binder is a mixture of glycerin and urea.

19. The product according to claim 18 wherein the binder is present in an amount of from about 1 to about 40 percent based on the weight of the product.

20. The product according to claim 15 wherein the fibers comprise wood pulp.

21. A fibrous product comprising:

fibrous material comprising individualized fibers having a hydrogen bonding functionality;

particles having a hydrogen bonding or a coordinate covalent bond forming functionality; and a binder selected from the group consisting of glycerin, a glycerin monoester, a glycerin diester, a propylene glycol, urea, and combinations thereof, the binder comprising binder molecules, the binder molecules having at least one functional group capable of forming a hydrogen bond or a coordinate covalent bond with the particles, and at least one functional group capable of forming a hydrogen bond with the fibrous material, wherein at least a portion of the particles are bound to the fibrous material.

22. The product of claim 21 wherein the binder comprises glycerin or urea.

23. The product according to claim 21 wherein the binder is selected from the group consisting of a glycerin monoester, a glycerin diester, and combinations thereof.

24. The product according to claim 21 wherein the binder comprises glycerin, urea, and combinations thereof.

25. The product according to claim 24 wherein glycerin comprises from about 40 to about 100 weight percent of the binder.

26. The product of claim 21 wherein the binder is selected from the group consisting of glycerin, a glycerin monoester, a glycerin diester, a propylene glycol, and combinations thereof.

27. The product of claim 21 wherein the binder is selected from the group consisting of a glycerin monoester, a glycerin diester, urea, and combinations thereof.

28. The product of claim 21 wherein the particles are soluble in water and are sparingly soluble in the binder.

29. The product of claim 21 wherein the particles comprise superabsorbent particles.

30. The product of claim 21 in the form of a web having a density of from 0.06 to 0.7 g/cc.

31. A fibrous product according to claim 21 wherein the fibrous material comprises individualized, high bulk fibers having intrafiber covalent bonds wherein the fibers have hydrogen bonding functionalities.

32. A product according to claim 31 having a density of from 0.06 g/cc to 0.7 g/cc.

33. An absorbent article comprised of the fibrous product of claims 1, 15, 16, 17, 18, 20, 21, 22, 24, 26, 27, 29, 31 or 32.

34. Binder coated fibers that will adhere to particles having a hydrogen bonding functional site or a coordinate covalent bonding functional site, comprising:
   individualized fibers that have a hydrogen-bonding functional site; and
   a binder selected from the group consisting of glycerin, a glycerin monoester, a glycerin diester, urea, a propylene glycol, and combinations thereof, the binder comprising binder molecules, the binder molecules having a functional group that is capable of forming at least one hydrogen bond with the fibers, and at least one functional group that is capable of forming a hydrogen bond or coordinate-covalent bond with particles, the binder being present in a sufficient amount to bond at least a portion of the particles to the fibers.

35. A fiber product produced by the method comprising the steps of:
   providing fibrous material comprising individualized fibers having a hydrogen bonding functionality;
   providing particles having a hydrogen bonding functionality or a coordinate covalent bond forming functionality;
   selecting a binder from the group consisting of glycerin, a glycerin monoester, a glycerin diester, a propylene glycol, urea, and combinations thereof, the binder comprising binder molecules, the binder molecules having at least one functional group capable of forming a hydrogen bond or a coordinate covalent bond with the particles, and at least one functional group capable of forming a hydrogen bond with the fibrous material; and
   spraying the binder on the fibers as the particles are being combined with the fibrous material, the binder being sprayed in sufficient amounts to bind a substantial portion of the particles to the fibrous material.

36. A fiber product produced by the method comprising the steps of:
   providing fibrous material comprising individualized fibers having a hydrogen bonding functionality;
   providing particles having a hydrogen bonding or a coordinate covalent bond forming functionality;
   selecting a binder from the group consisting of glycerin, a glycerin monoester, a glycerin diester, urea, and combinations thereof; and
   exposing at least a portion of the particles to sufficient amounts of the binder in the presence of the fibrous material under conditions that favor the formation of non-covalent bonds to bind at least a portion of the particles to the fibrous material.

* * * * *